(12) United States Patent
Loskutoff

(10) Patent No.: US 7,273,694 B2
(45) Date of Patent: Sep. 25, 2007

(54) METHOD AND APPARATUS FOR REDUCING PATHOGENS IN A BIOLOGICAL SAMPLE

(75) Inventor: Naida M. Loskutoff, Omaha, NE (US)

(73) Assignee: Safety Art, LLC, Omaha, NE (US)

( * ) Notice: Subject to any disclaimer, the term of this patent is extended or adjusted under 35 U.S.C. 154(b) by 507 days.

(21) Appl. No.: 10/478,917

(22) PCT Filed: May 21, 2002

(86) PCT No.: PCT/US02/16082

§ 371 (c)(1),
(2), (4) Date: Nov. 21, 2003

(87) PCT Pub. No.: WO02/094739

PCT Pub. Date: Nov. 28, 2002

(65) Prior Publication Data

US 2005/0079480 A1    Apr. 14, 2005

Related U.S. Application Data

(60) Provisional application No. 60/292,723, filed on May 21, 2001, provisional application No. 60/293,249, filed on May 24, 2001, provisional application No. 60/293,713, filed on May 25, 2001, provisional application No. 60/294,196, filed on May 29, 2001, provisional application No. 60/295,255, filed on Jun. 1, 2001.

(51) Int. Cl.
*A01N 1/02* (2006.01)
*C12N 5/00* (2006.01)
*C07G 15/00* (2006.01)

(52) U.S. Cl. ............................ 435/2; 435/268; 435/325

(58) Field of Classification Search ...................... None
See application file for complete search history.

(56) References Cited

U.S. PATENT DOCUMENTS

| | | | |
|---|---|---|---|
| 5,770,363 A * | 6/1998 | Brown | 435/6 |
| 6,140,121 A | 10/2000 | Ellington et al. | 435/374 |
| 6,248,588 B1 * | 6/2001 | Crespo et al. | 435/404 |
| 6,671,558 B1 * | 12/2003 | Soykan et al. | 607/50 |
| 2005/0064579 A1 * | 3/2005 | Loskutoff et al. | 435/283.1 |

OTHER PUBLICATIONS

"Identification and Distribution of Pz-peptidases A and B in Human Semen" by Bruce A Lessley, et al., Journal of Andrology, Nov./Dec. 1985, vol. 6, pp. 372-378; from the Department of Physiological Sciences, Oklahoma State University, Stillwater, Oklahoma.

"Sperm Recovery Techniques to Maximize Fertilizing Capacity" by David Mortimer, Reprod. Fertil. Dev., 1994, 6, pp. 25-31.

"Identification and Subcellular Localization of the Enzymes Effecting Penetration of the Zona Pellucida by Rabbit Spermatozoa" by Richard Stambaugh, et al, F. Reprod. Fert. 1969 19, pp. 423-432; Division of Reproductive Biology, Department of Obstetrics and Gynecology, University of Pennyslvania School of Medicine, Philadelphia, PA 19104.

* cited by examiner

*Primary Examiner*—Christopher R. Tate
(74) *Attorney, Agent, or Firm*—Suiter Swantz pc llo

(57) ABSTRACT

The present invention is directed to a method and apparatus for disinfection of biological samples, including semen and the like. In a first aspect of the present invention, a method for reducing pathogens in a biological sample includes passing the biological sample through a gradient including an enzyme suitable for removal of at least one pathogen from the sample. In an additional aspect of the present invention, an apparatus for removing pathogens from a biological sample includes a container including a gradient having at least one layer that is suitable for having the biological sample pass through the layer, the at least one layer including an enzyme suitable for removing at least one pathogen from the biological sample.

12 Claims, 25 Drawing Sheets

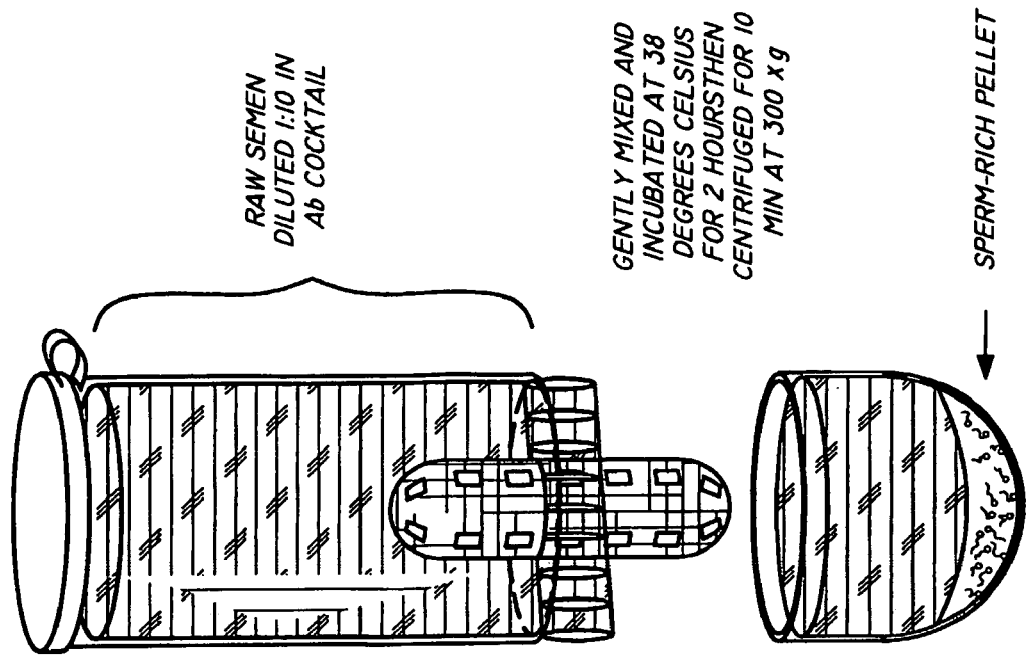
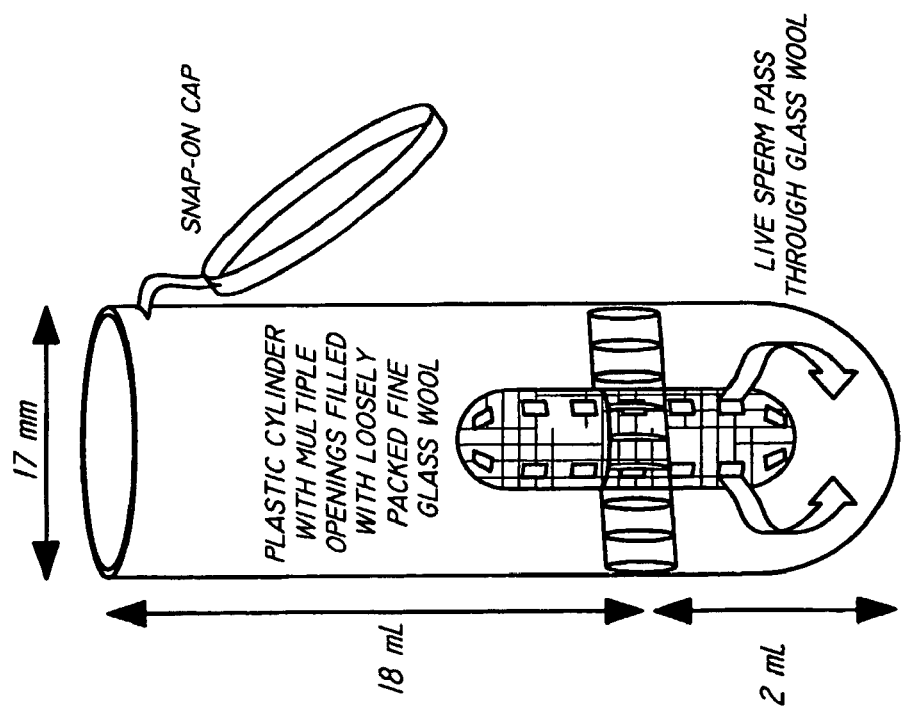
FIG. 11A

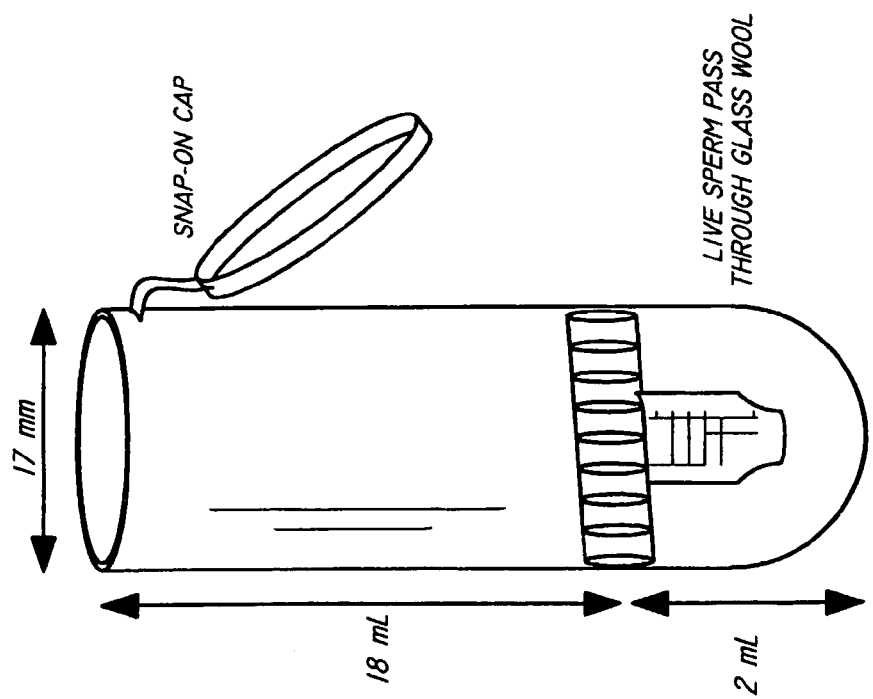
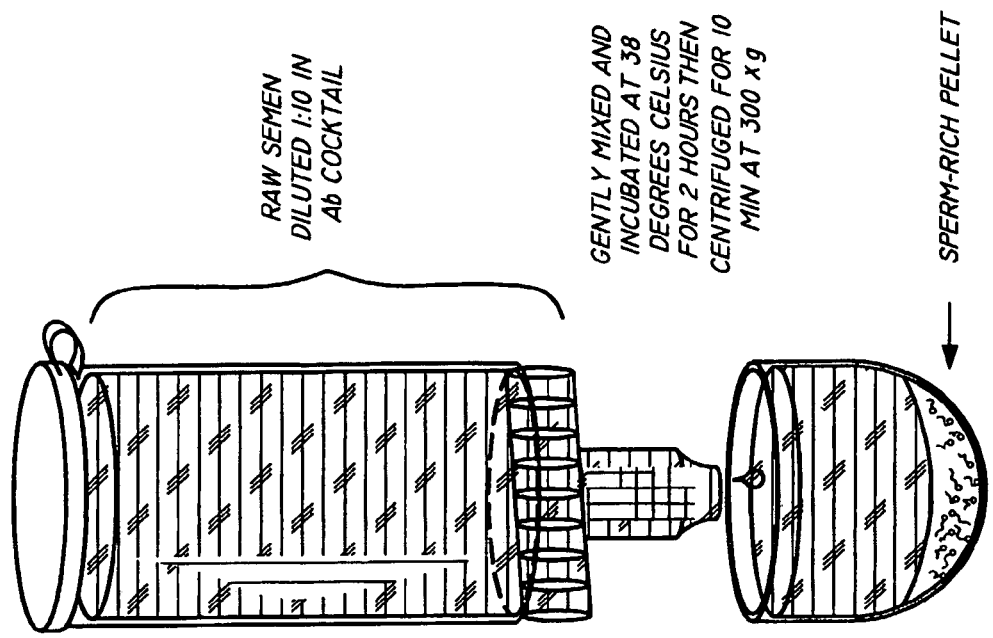
FIG. 11B

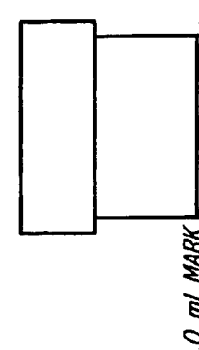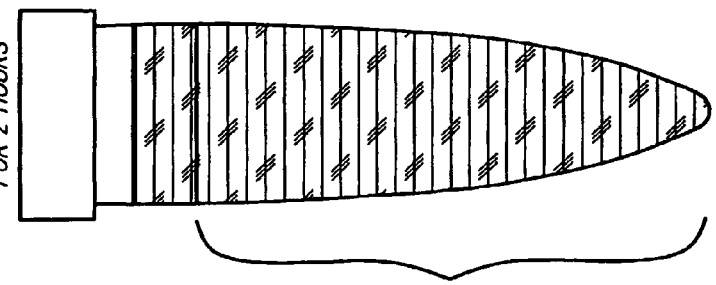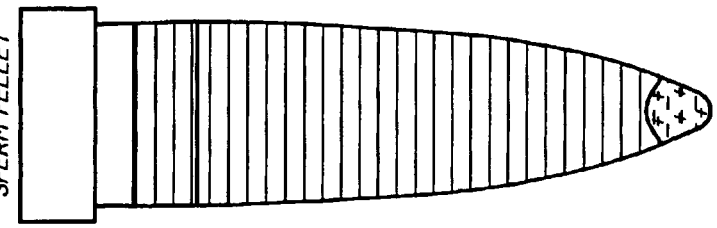
FIG. 12

DOSE-RESPONSE OF DECREASING CONCENTRATIONS OF SOY-BASED TRYPSIN INACTIVATOR IN 90% ISOLATE ON ITS ABILITY TO DETACH CONFLUENT BRL MONOLAYERS

− = NO DETACHMENT NOTED (TRYPSIN INACTIVE);
+ = CELLS DETACHING (TRYPSIN ACTIVE)

LOWEST EFFECTIVE DOSE: 10 ug/mL

| SOY TRYPSIN INACTIVATOR mg/mL: | 1.4 (n=1) | 0.35 (n=1) | 0.15 (n=1) | 0.08 (n=1) | 0.02 (n=1) | 0.01 (n=3) | 0.005 (n=3) | 0.0025 (n=1) | 0.0006 (n=1) |
|---|---|---|---|---|---|---|---|---|---|
| 0.25% TRYPSIN | − | − | − | − | − | 1. −<br>2. −<br>3. − | 1. −<br>2. −<br>3. ROUNDED AT 5 MIN; >90% DETACHED AT 10 MIN | +<br>ROUNDED AT 3 MIN | +<br>ROUNDED AT 3 MIN; >90% DETACHED AT 10 MIN |
| 0.125% TRYPSIN | − | − | − | − | − | 1. −<br>2. −<br>3. − | 1. −<br>2. −<br>3. ROUNDED AT 5 MIN; >90% DETACHED AT 10 MIN | | +<br>ROUNDED AT 3 MIN; >90% DETACHED AT 10 MIN |

FIG. 15

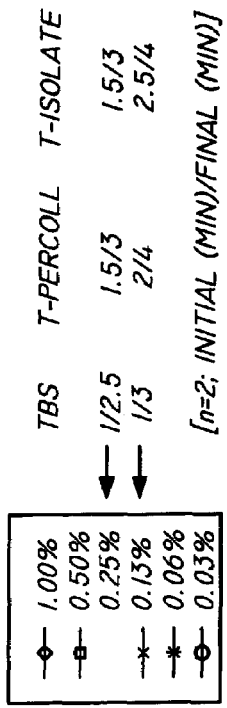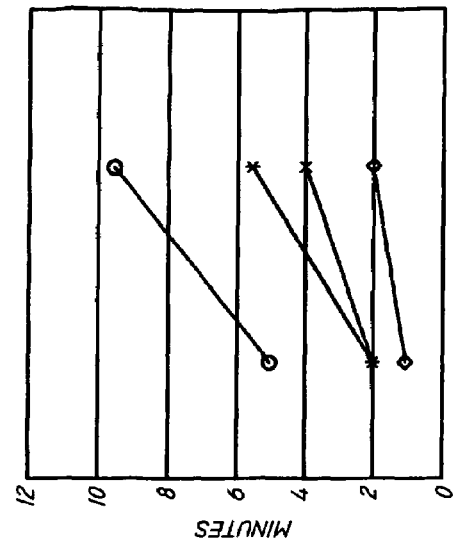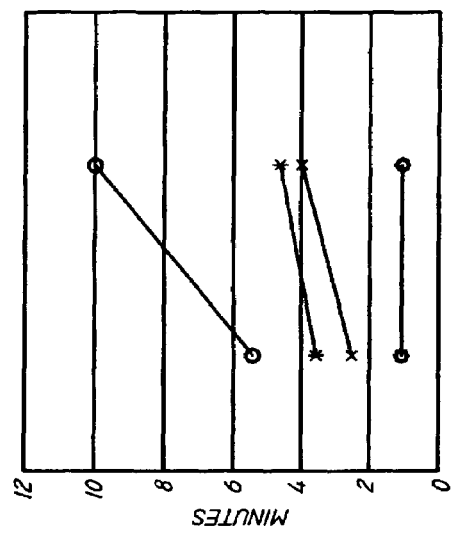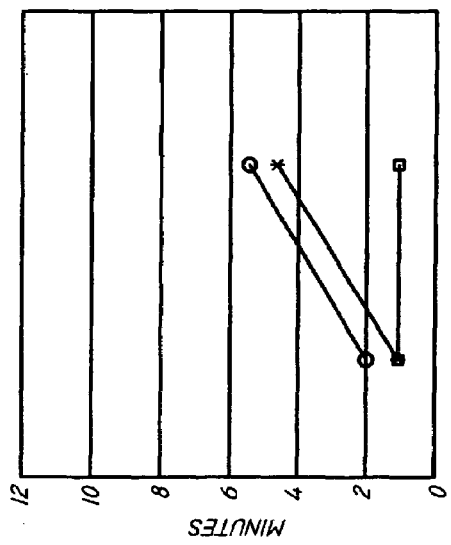
FIG. 16

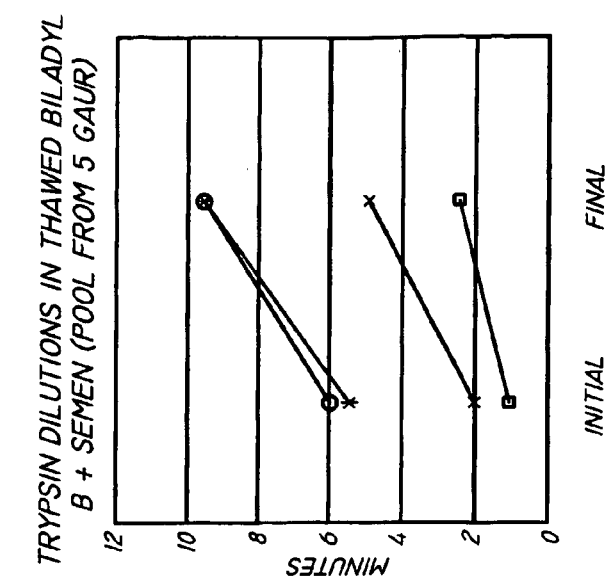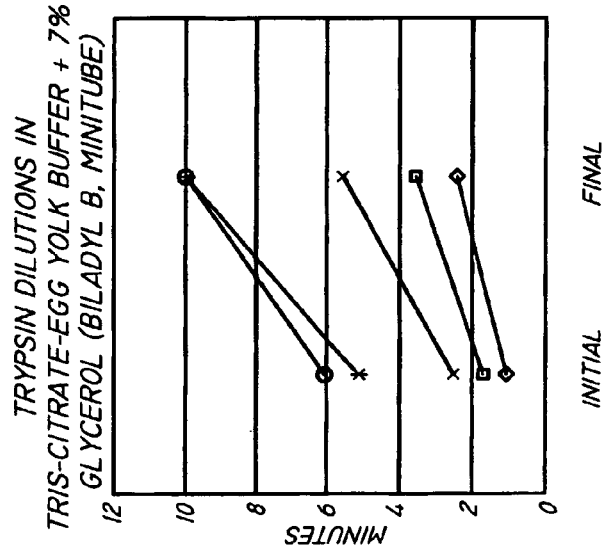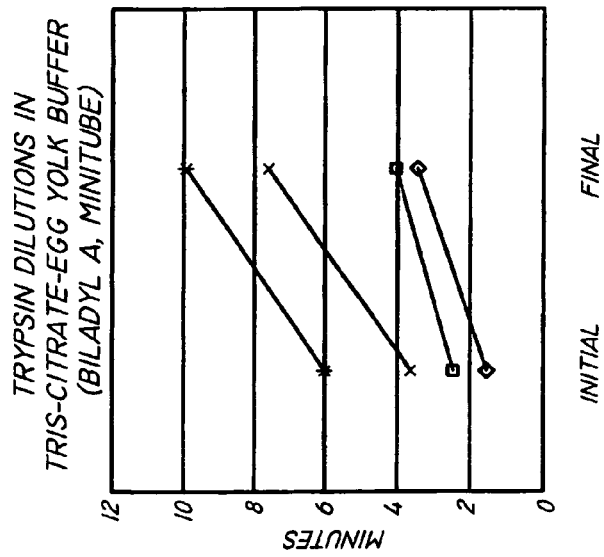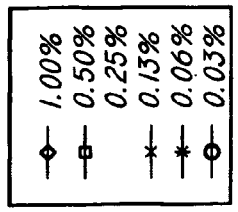
FIG. 17

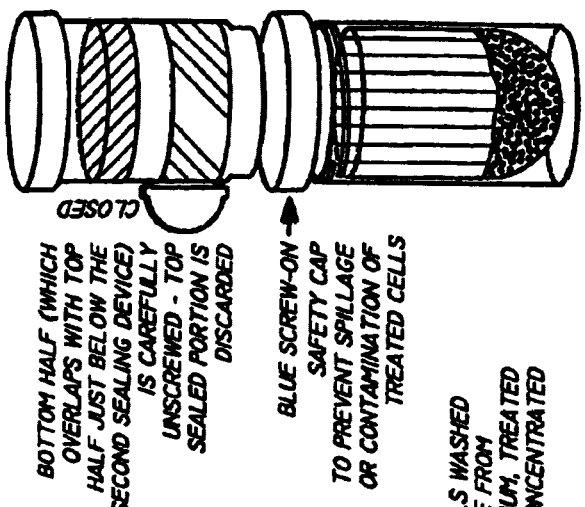
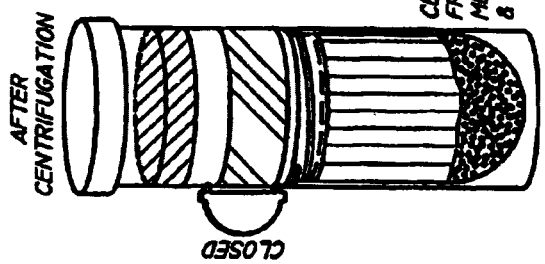
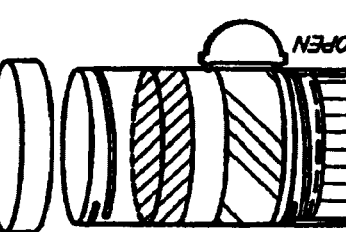
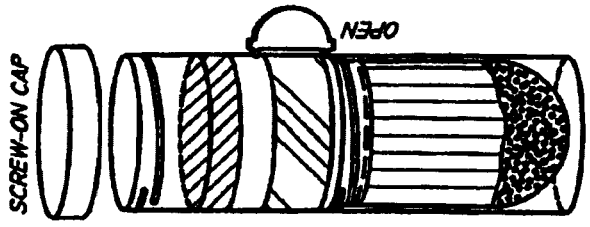
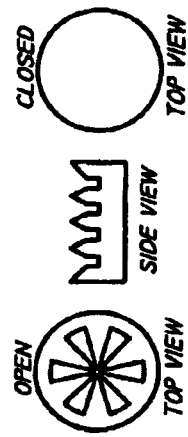
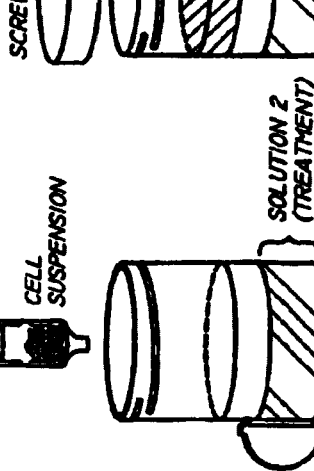
FIG. 18

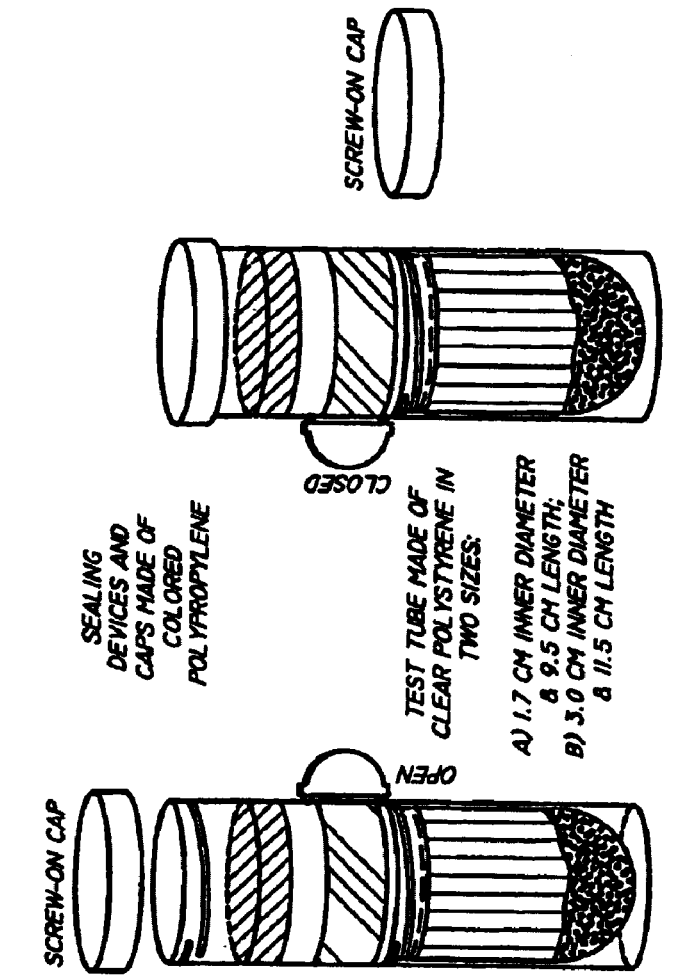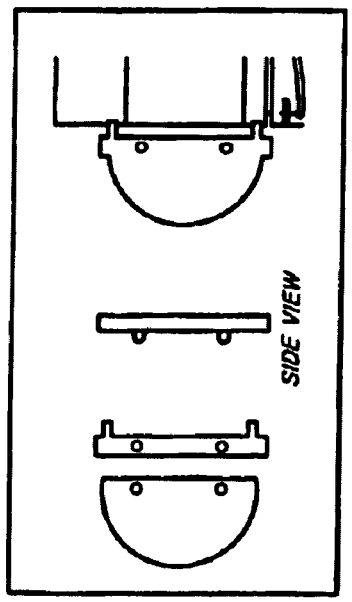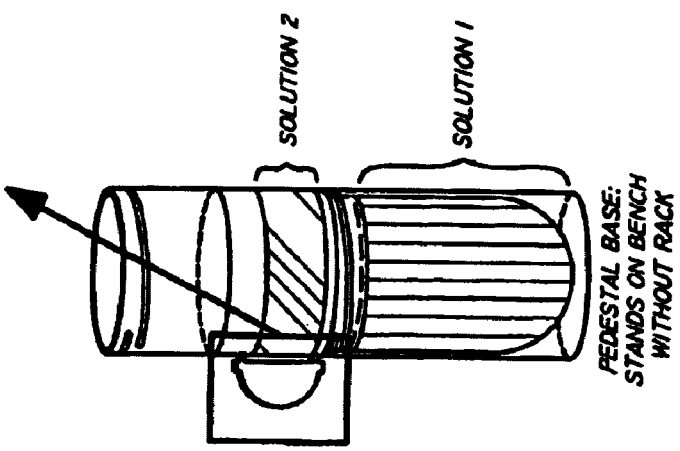
FIG. 19

METHOD AND APPARATUS FOR REDUCING PATHOGENS IN A BIOLOGICAL SAMPLE

CROSS REFERENCE TO RELATED APPLICATIONS

The present application claims priority under 35 U.S.C. §119(e) to U.S. patent application Ser. No. 60/292,723, filed May 21, 2001, U.S. patent application Ser. No. 60/293,249, filed May 24, 2001; U.S. patent application Ser. No. 60/293,713, filed May 25, 2001; U.S. patent application Ser. No. 60/294,196, filed May 29, 2001; and U.S. patent application Ser. No. 60/295,255, filed Jun. 1, 2001, which are herein incorporated by reference in their entirety.

FIELD OF THE INVENTION

The present invention generally relates to the field of contamination by pathogens of biological samples, and particularly to an apparatus and method for removal of pathogens from seminal fluid.

BACKGROUND OF THE INVENTION

The present invention generally relates to the field of contaminate reduction in seminal fluid, and more particularly to a process to reduce or eliminate pathogenic contamination in seminal fluid.

A great risk exists concerning transmission of pathogenic agents in biological samples. Effective processes to reduce or eliminate contamination (herein after "decontamination") in biological samples have generally been developed for embryos. The embryo has an outer layer, called the zona pellucida, which is impenetrable to a variety of pathogenic agents; however, it is still possible to transmit disease by pathogens adhering to the surface of the zona pellucida. Because of the relatively large size of embryos and oocytes (typically on the order of 100 micrometers in diameter), they can be handled individually and treated (or "dipped") in a decontamination solution (e.g., containing a low concentration of a proteolytic enzyme such as trypsin) which effectively inactivates many infectious agents. Trypsin treatment is harsh and can irreversibly damage embryos if overexposed.

Sperm, on the other hand, cannot be handled individually (the diameter of sperm heads typically are less than 5 micrometers) so it has not been possible to treat sperm by a brief exposure of typsin treatment without causing damage.

For the forgoing reasons, there is a need for a process that decontaminates seminal fluid of both bacteria and viruses, which may allow the reduction or elimination of pathogenic agents from a biological sample, such as seminal fluid.

SUMMARY OF THE INVENTION

Accordingly, the present invention is directed to a method and apparatus for disinfection of biological samples, including semen and the like. For instance, the present invention includes a process for decontamination of biological samples, including seminal fluid, such as through the use of a two-step decontamination method: first, seminal fluid is incubated in a novel antibiotic cocktail capable of decontaminating a variety of microorganisms, including bacteria. The sperm are then concentrated by gentle centrifugation to obtain a pellet of decontaminated sperm cells.

Second: the present invention is further directed to be a process by which virus decontamination of seminal fluid, previously treated with the antibiotic cocktail or not, may be accomplished by centrifuging the fluid through coated silica particle gradients which may include: enzyme and enzyme inhibitor to obtain a pellet of decontaminated sperm cells. The step serves to inactivate free viruses and remove somatic cells that may contain viruses and could have been present in the seminal fluid The present invention is further directed to be processed using a column, kit, or the like to perform both the bacteria and/or virus decontamination.

A previous attempt to decontaminate sperm by adding trypsin directly to the semen was not conclusive nor fully tested. Firstly, seminal plasma contains proteins which could inactivate trypsin. Furthermore, the results of those previous studies were based on viral assays that are outdated as compared to some of the more recent assays (e.g., detecting viruses by polymerase chain reaction methods) were are highly sensitive.

In one embodiment of the present invention, a gradient of silica particles coated with either polyvinylpyrrolidone or silane is utilized: one layer containing active trypsin that the sperm are passed through by gentle centrifuation (700×g for 30 min) into a second layer containing a soy-based trypsin inactivator. This improvement is useful in that it: (1) protects the sperm from damage by providing only a brief exposure to the trypsin, (2) the trypsin can eliminate any free infectious agents that are associated or adhered to the sperm, (3) separates the dead and damaged sperm from the live, treated sperm (density gradient centrifugation is commonly used for this purpose in andrology and in vitro fertilization practices) and (4) somatic cells (which can contain pathogenic agents) are separated and removed from the treated lives sperm because they can not pass into the final gradient using the gentle centrifugal force used in the procedure (live sperm do pass through because of their progressive forward motility).

There are currently no known processes that combine a density gradient centrifugation system with an enzyme treatment to decontaminate sperm. Furthermore, there are currently no products available that would allow direct access of the treated sperm sample (which is on the bottom of a tube containing the multiple gradients) without going through the upper (and potentially contaminated) layers, either directly to the bottom to aspirate the treated sperm, or by aspirating and discarding the upper layers down to the treated sperm.

These techniques are inherently flawed for any decontamination procedure because of the likelihood of transferring infectious agents back to the treated sperm sample (e.g., directly from the pipette or indirectly from contaminated materials running down the side of the tube during aspiration). An important feature of this invention, therefore, is the design of novel plasticware that will facilitate the layering of the density gradients and semen, treatment of the semen, then isolation of the treated sperm from the contaminated material which can be safely removed and discarded as biohazardous waste.

The Certified Semen Services (CSS), a wholly owned subsidiary of the National Association of Animal Breeders (NAAB), established a method for bacteria decontamination in semen. The process is greatly improved upon in this invention. The present invention uses a higher concentration of antibiotics, and an additional antibiotic, which makes the cocktail of antibiotics more effective to inactivate a variety of bacteria and other susceptible microorganisms. In addition, in the CSS's published processing time for the contact between the semen and the antibiotic cocktail is only three to five minutes at room temperature. The effectiveness of this decontamination process is questionable because decreased temperature decreases bacteria metabolism and thus antibiotic reaction. In addition, the extremely short time period (3-5 min) the bacteria is exposed to the antibiotic is also likely not effective because it takes longer than that for bacteria to divide (the time when the antibiotics exert their effects).

The present invention relieves this problem, in an embodiment, by incubating semen in the novel antibiotic cocktail solution for a minimum of 2 hours at physiological temperature. By changing those parameters, the metabolism of the bacteria and the subsequent inactivation should be more effective and more useful. The sperm are concentrated by gentle centrifugation (300×g for 10 min) at the conclusion of the incubation in the antibiotic cocktail.

It is the intention of the present invention to present a process by which to reduce contamination in seminal fluid. By providing a process to decontaminate seminal fluid, more sources of seminal fluid may be used for different techniques, which gives it a wide range of applicability and utility. The process may be used in human semen decontamination and especially for those pathogens that are known to be transmitted sexually and are a great health concern, e.g. viruses such as HIV, Hepatitis B and C, which may be reduced or eliminated. This invention may allow infected men to participate in procedures such as artificial insemination, in-vitro fertilization, and other suitable applications in assisted reproductive technology potentially without transmitted such infectious agents to their spouses, unborn children as well as to health care workers handling the contaminated semen samples.

This invention can also be used in animal or livestock industries. The potential exists to infect both a fetus and a mother through pathogen-infected sperm. Recently, the threat of pathogenic agents being transported internationally has greatly lessened the ability to import sperm cells. In livestock, viruses such as foot-and-mouth disease virus and porcine reproductive and respiratory syndrome (PRRS) virus have shown to have devastating consequences to the national and international agricultural economies. As a result of such disease outbreaks, there have been stricter regulations and sometimes bans on importation of animals or semen are becoming more frequent, which affects animal and livestock industries by cutting off supplies and sources of new genetic materials. This invention may be able to reduce or eliminate pathogenic agents from seminal fluid. This would allow seminal fluid to be safely transported around the world. This is in light of the precedent set by the trypsin treatment procedure for processing embryos which has, as a consequence, permitted the lessening of regulatory restrictions (e.g., USDA) for the international transport of livestock (mostly cattle) embryos since research has shown that the risk of transmitting specific infectious agents by embryo transfer is minimal if they embryos are properly treated.

By allowing international transport, this invention will also give zoos and conservation projects opportunity to import sperm from other countries with the reassurance that the seminal fluid is not infected with pathogens. This may help diversity and conservation of animal life—which include the germplasm of rare and/or endangered livestock breeds for germplasm banking programs throughout the world, including the USA (e.g., USDA Agricultural Research Services, National Animal Germplasm Program).

In a first aspect of the present invention, a method for reducing pathogens in a biological sample includes passing the biological sample through a gradient including an enzyme suitable for removal of at least one pathogen from the sample.

In an additional aspect of the present invention, an apparatus for removing pathogens from a biological sample includes a container including a gradient having at least one layer that is suitable for having the biological sample pass through the layer, the at least one layer including an enzyme suitable for removing at least one pathogen from the biological sample.

In a further aspect of the present invention, an apparatus for removing pathogens from a biological sample includes a container having a means for limiting exposure of a biological sample to an enzyme, the enzyme suitable for removing at least one pathogen from the biological sample.

It is to be understood that both the forgoing general description and the following detailed description are exemplary and explanatory only and are not restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which:

FIG. 11A is an illustration of an apparatus operable to embody the present invention in which an antibiotic cocktail treatment is shown;

FIG. 11B is an illustration of an apparatus operable to embody the present invention in which an antibiotic cocktail treatment is shown;

FIG. 12 is an illustration of an apparatus and method of an embodiment of the present invention in which a treatment for boar semen is shown;

FIG. 15 is a table illustrating dose-response of decreasing concentration of soy-based trypsin inactivator in 90% isolate on its ability to detach confluent BRL monolayers;

FIG. 16 includes graphical depictions of trypsin activity after dilution and time for confluent buffalo rat liver cell monolyaers to detach after exposure and incubation at 38 degrees Celsius;

FIG. 17 includes graphical depictions of trypsin activity after dilution and time for confluent buffalo rat liver cell monolyaers to detach after exposure and incubation at 38 degrees Celsius;

FIG. 18 is an illustration of an exemplary embodiment of the present invention wherein an apparatus in accordance with an aspect of the present invention is shown;

FIG. 19 is an illustration of an exemplary embodiment of the present invention wherein an apparatus in accordance with an aspect of the present invention is shown;

DETAILED DESCRIPTION OF THE INVENTION

Figure 2B:
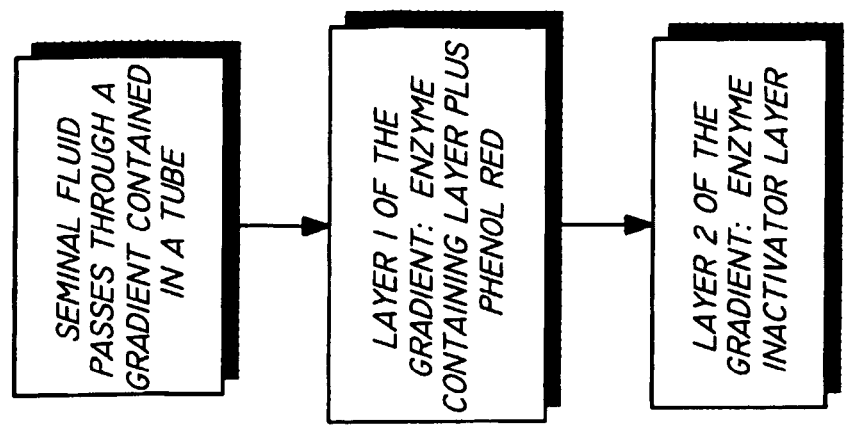
FIG. 2B is a flow chart illustrating an exemplary method of the present invention wherein a gradient including an enzyme is utilized.

Reference will now be made in detail to the presently preferred embodiments of the invention, examples of which are illustrated in the accompanying drawings.

Referring generally now to FIGS. 1 through 23, exemplary embodiments of the present invention are shown. The impetus for the development of this procedure began on 24 Sep. 1999 at the Wild Cattle and Buffalo Taxon Advisory Group (TAG) meeting that was held at the annual conference of the American Zoo and Aquarium Association (AZA) in Minneapolis, Minn. At that meeting, a call was made for the formation of a task force by reproductive biologists collaborating or working directly with zoos to increase the research and development of assisted reproductive techniques (e.g., artificial insemination and embryo transfer) for non-domestic animals.

The reason for the alarm was that assisted reproductive technology may soon become the only means possible that the USDA Animal and Plant Health Inspection Service (APHIS) will allow the importation of new genetic lines for captive ungulates (hoofed species such as antelope, deer, buffalo, and the like) and suids (exotic pig species) in American zoos. At that time, there was major concern over news that the last quarantine station that was available for the USDA-mandated quarantine period (60 days outside the USA, followed by 30 days within the USA) for animals exported from Africa and Asia, may soon close (the station is in Poland—and news that this country was going to join the European union meant that they would be required to follow German guidelines which, consequently, would not permit the entry of these animals).

As a result of this revelation, the decision was made to focus more research on pathogen (e.g., microorganisms and viruses that create disease) interactions with the spermatozoa and embryos of wildlife species. It was realized that there had been research successfully conducted in the development of methods for "disinfecting" embryos (of specific pathogens). This research has had a direct effect on the OIE—and, as a consequence, the USDA APHIS, in lowering restrictions for the international movement of embryos, so long as the IETS HASAC guidelines were followed for proper embryo handling and treatment. See *Manual of the International Embryo Transfer Society: A Procedural Guide and General Information for the Use of Embryo Transfer Technology Emphasizing Sanitary Procedures* (3rd Edition), D. A. Stringfellow and S. M. Seidel, Editors, IETS, Savoy, Ill., USA, which is herein incorporated by reference in its entirety.

However, it was apparent that although there were reports on research concerning pathogen interactions with embryos (and predominantly with bovine embryos), there was a paucity of information on pathogen interactions with semen or spermatozoa (for any species). Therefore, the present invention developed procedures for "disinfecting" semen, i.e. substantially reducing and even eliminating pathogens from biological samples, which has significance for humans and livestock in addition to zoo animals and wildlife.

Although procedures exist to reduce or eliminate contamination in oocytes and embryos, and are beneficial to preventing the spread of pathogenic agents, these procedures are not appropriate for use with seminal fluid. Oocytes have a protective coating, the zona pellucida, which protects the oocytes from the damaging effects of the pathogen reducing or eliminating procedures. Sperm do not have a similar protective coating and may be damaged by the current procedures.

The present invention addresses these problems by identifying a new and successful process to decontaminate seminal fluid. The procedure does not damage the sperm acrosome; therefore, the sperm cells remain functional. This invention may be useful in a variety of application such as decontamination of seminal fluid for propagation of livestock, international animal semen transport and other animal applications. In addition, the invention may be useful in decontamination of human semen containing pathogens that are transmitted sexually and a great health concern, including viruses such as HIV, Hepatitis B and C, and other pathogenic agents which may be reduced or eliminated.

Figure 2A:
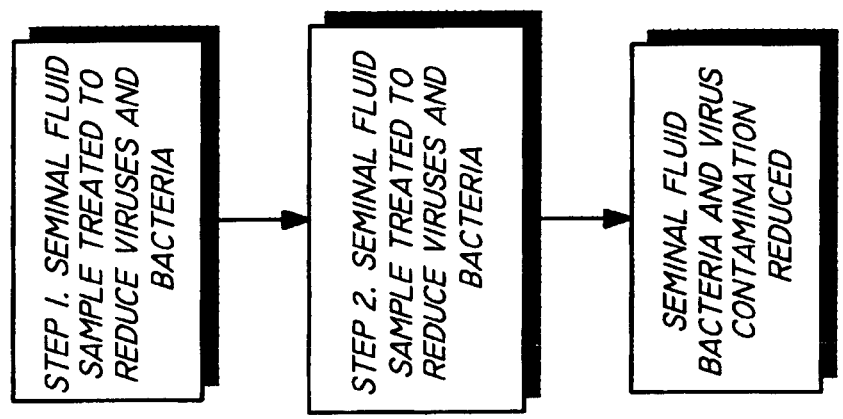
FIG. 2A is a flow chart illustrating an exemplary method of the present invention.
Figure 1:
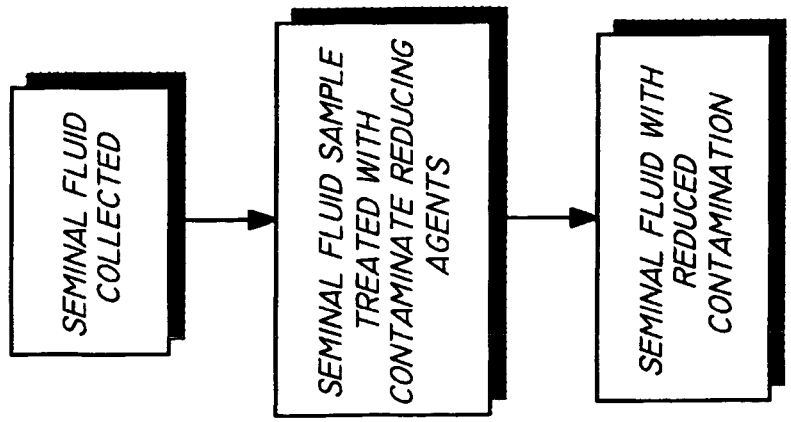
FIG. 1 is a flow chart illustrating an exemplary method of the present invention.

In FIG. 1, an exemplary embodiment of the present invention is shown. Seminal fluid is treated with decontamination agents. These agents are effective and sperm remain functional. The invention is not limited to the agents described. Decontamination agents may be changed in order to treat for various pathogenic agents. These agents may consist of bacteria and/or virus decontamination agents (FIG. 2). The use of these agents may be performed in two steps: bacteria decontamination and virus decontamination.

Alternately, either process may take place by itself depending on the use in the art as desired by a person of ordinary skill in the art.

Unlike embryos that are large enough to be handled individually (i.e., placed into, then taken out of a solution) using specialized instrumentation (e.g., micropipettes), individual sperm are not. One challenge, therefore, was how to limit the exposure of sperm to the enzymatic activity in accordance with the process of the present invention, since prolonged exposure (e.g., greater than 90 sec) of embryos to trypsin may have detrimental effects on viability.

The invention may be used as a column, kit, or the like which may decontaminate seminal fluid. An exemplary embodiment of the virus decontamination process is shown in FIG. 2B. The seminal fluid, which may or may not have been treated with bacteria decontamination agents, is centrifuged through a gradient. The gradient may be a density gradient, which has been shown effective for washing human sperm. However, the use of enzymes in the process to decontaminate seminal fluid of viruses and/or bacteria is unique and has many unexpected benefits.

Figure 3A:
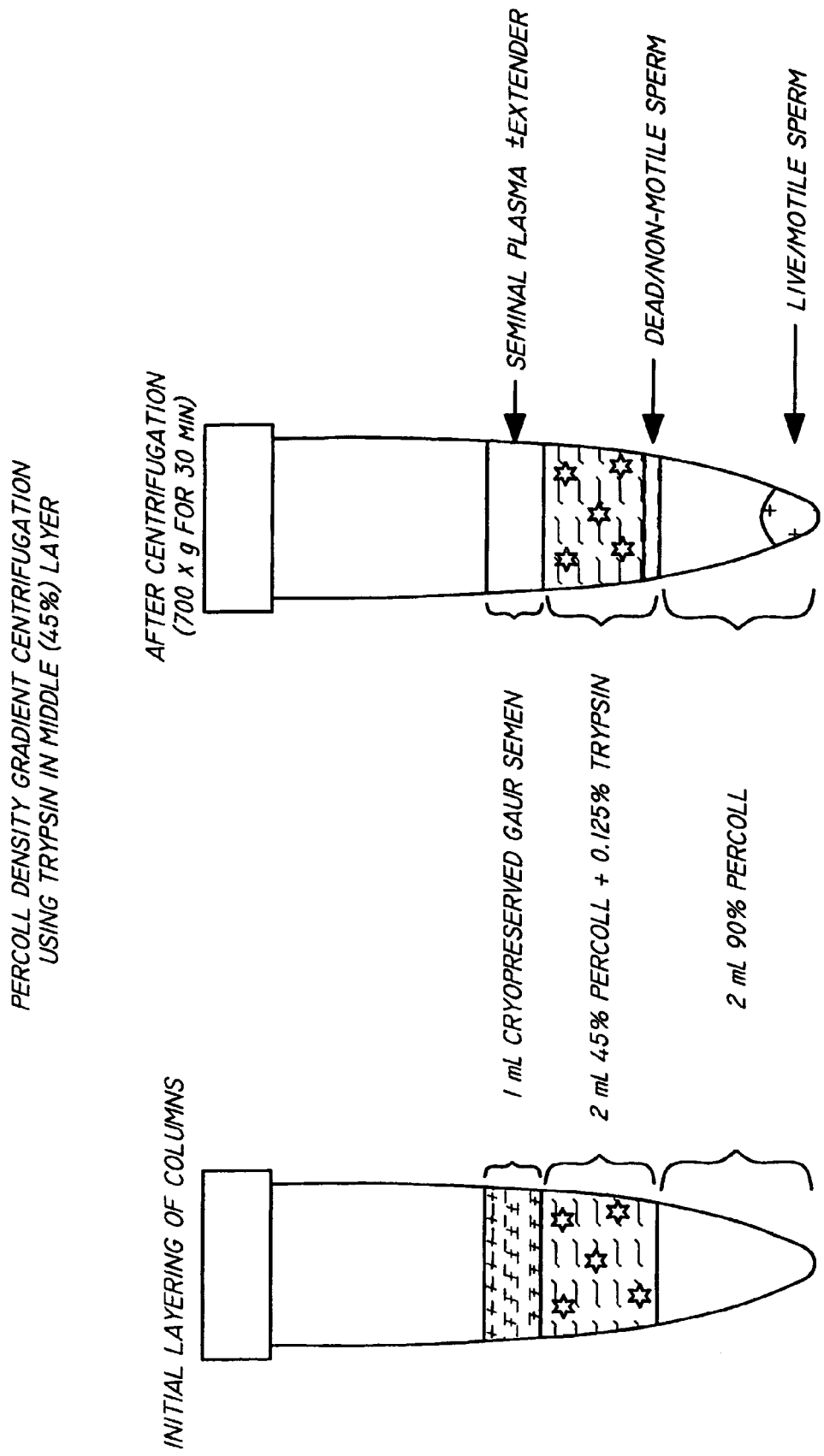
FIG. 3A is an illustration of an embodiment of the present invention in which a column is utilized, the column including 0.125% trypsin.
Figure 3B:
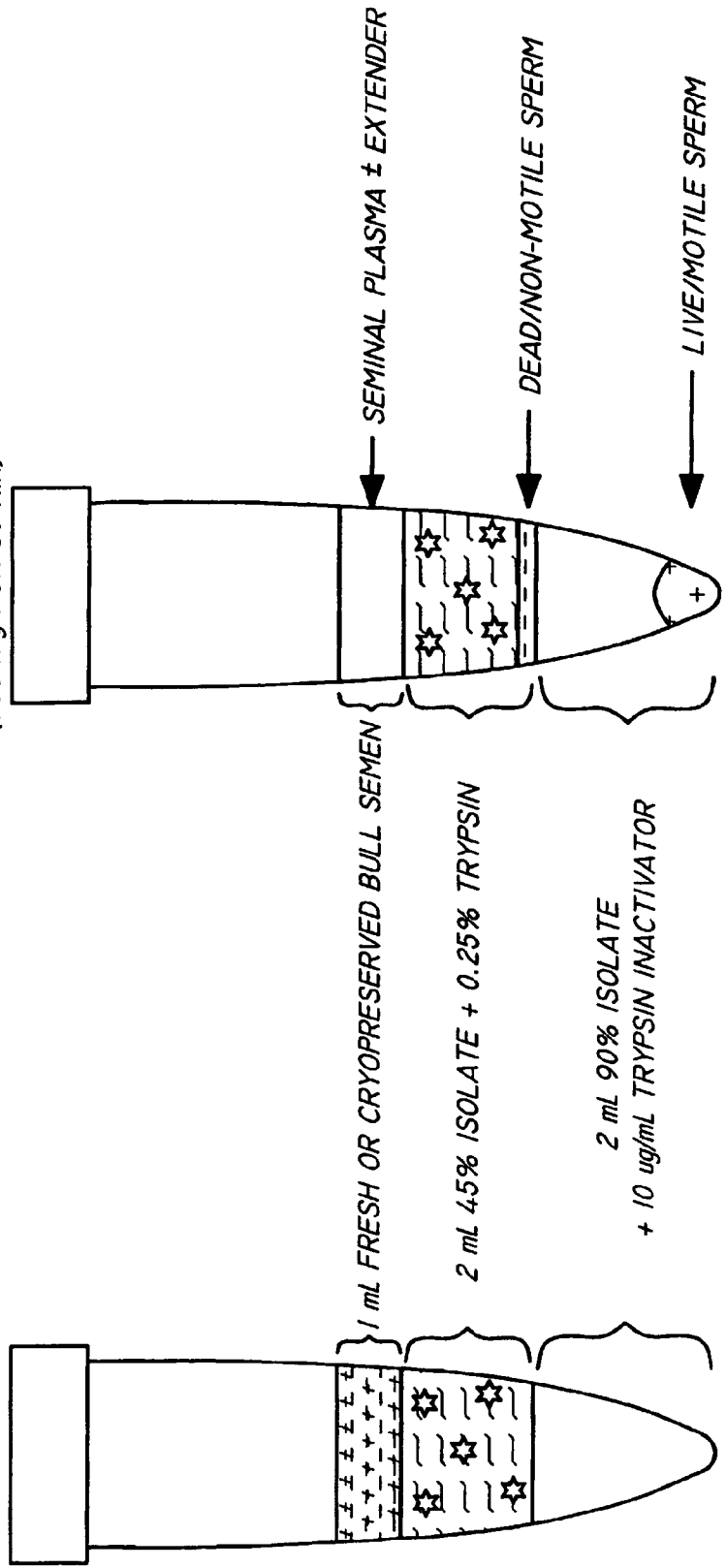
FIG. 3B is an illustration of an embodiment of the present invention in which a column is utilized, the column including 0.25% trypsin.

To address this criterion for the treatment of sperm by trypsin, protocols for processing semen were evaluated. Through experimentation, a density gradient centrifugation was tested in which sperm are exposed to different treatments (concentrations of PVP- or silane-coated silica particles), for providing a transitory treatment by trypsin. A series of experiments were conducted testing the viability cryopreserved bovine (*Bos gaurus*) sperm treating using a Percoll density gradient centrifugation, but with the addition of 0.125% trypsin in the middle (45% Percoll) layer, as shown in FIG. 3A. This initial testing incorporated trypsin at half the concentration recommended for use in embryos—in anticipation of potential detrimental effects to the sperm—and no inhibitor of trypsin was used in the final treatment (90% Percoll) layer. Later studies showed no detrimental effects of increasing the concentration of trypsin to 0.25%, so this was incorporated into the 45% silica particle layer in the modified protocol, along with the addition of a soy-based trypsin inhibitor in the final (90%) column which contained the treated sperm, as shown in FIG. 3B. The trypsin inhibitor may be utilized at a concentration of approximately 20 µg/ml. Another series of experiments were performed to ensure that the trypsin was not inactivated after dilution with the PVP-(Percoll) or silane-(Isolate) coated silica particles or after dilution with egg yolk-based cryodiluents with or without semen. Those results clearly showed that dilution of trypsin (for final effective concentrations of 0.125% and 0.25%) with any of these products did not diminish enzymatic activity (as determined by the detachment of confluent, somatic cell monolayers after direct exposure to the combinations containing trypsin), as depicted in FIGS. 16 & 17.

Figure 4:
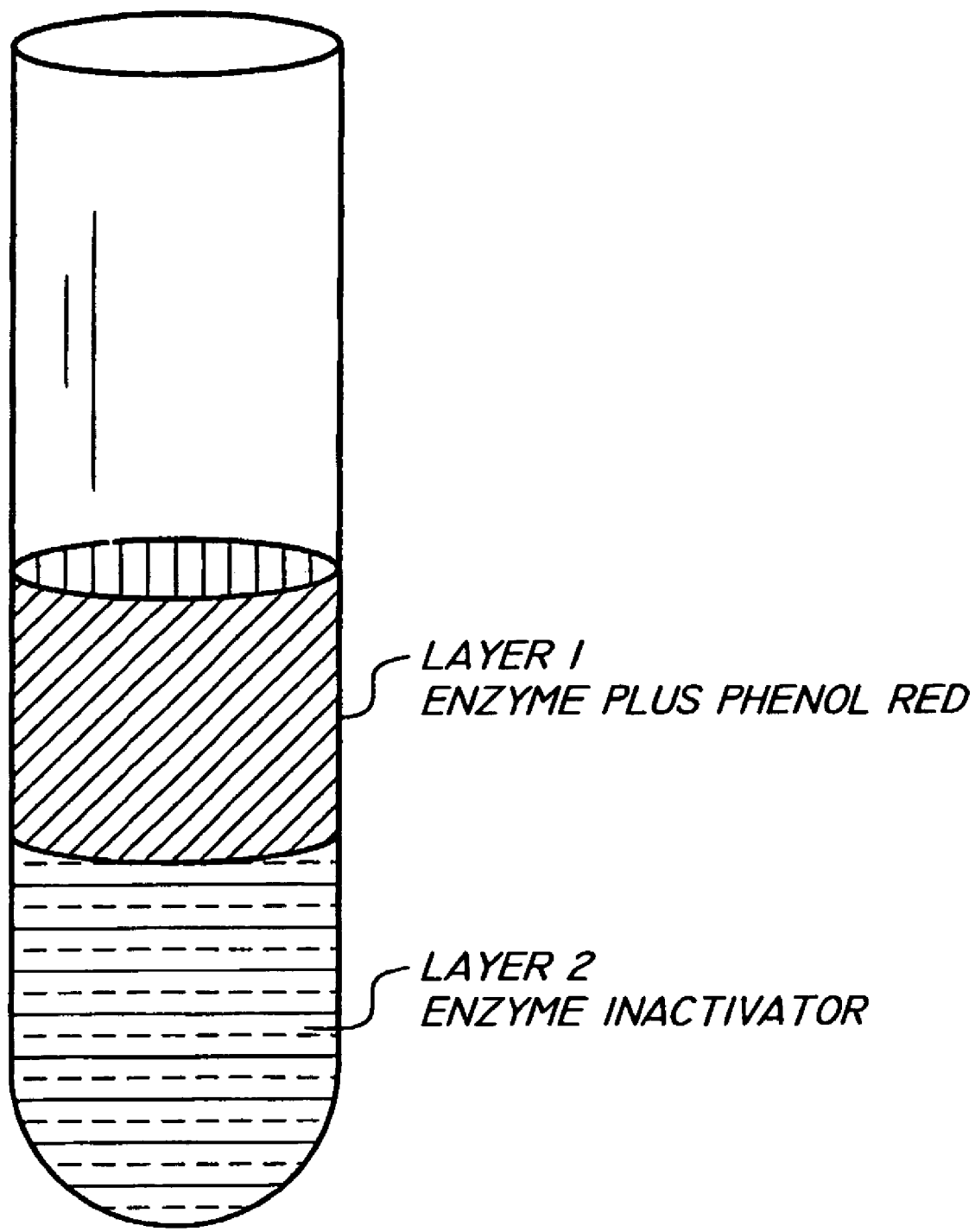
FIG. 4 is an illustration of a column operable to embody an apparatus of the present invention.

Referring now to FIG. 4, in this example, layer one is an enzyme containing layer plus colorant to distinguish it from layer 2. This enzyme is defined as anything that will be effective in inactivating a virus as a pathogenic agent. In addition, the colorant used is not limited to phenol red as used here. Any or no colorant may be used. Layer two contains an enzyme inactivator. Seminal fluid can only be exposed to enzyme for a certain amount of time before the sperm cells are damaged. The enzyme inactivator may eliminate this problem by stopping any reaction that is taking place between the sperm cells and enzyme, which may affect spermatozoal viability.

FIG. 4 shows an exemplary drawing of a column or the like which may be used to decontaminate seminal fluid. The decontamination may occur in a tube, series of tubes, or the like. In addition, the figure shows the layering effect of the gradient.

Figure 5:
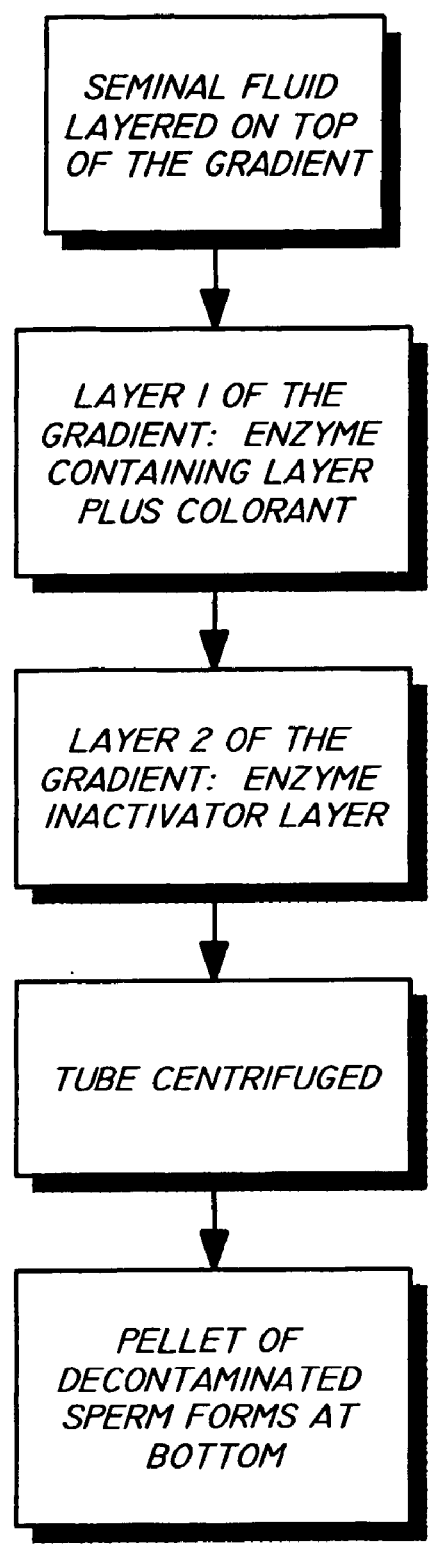
FIG. 5 is a flow diagram depicting an exemplary method of the present invention wherein a gradient including an enzyme is centrifuged.
Figure 6:
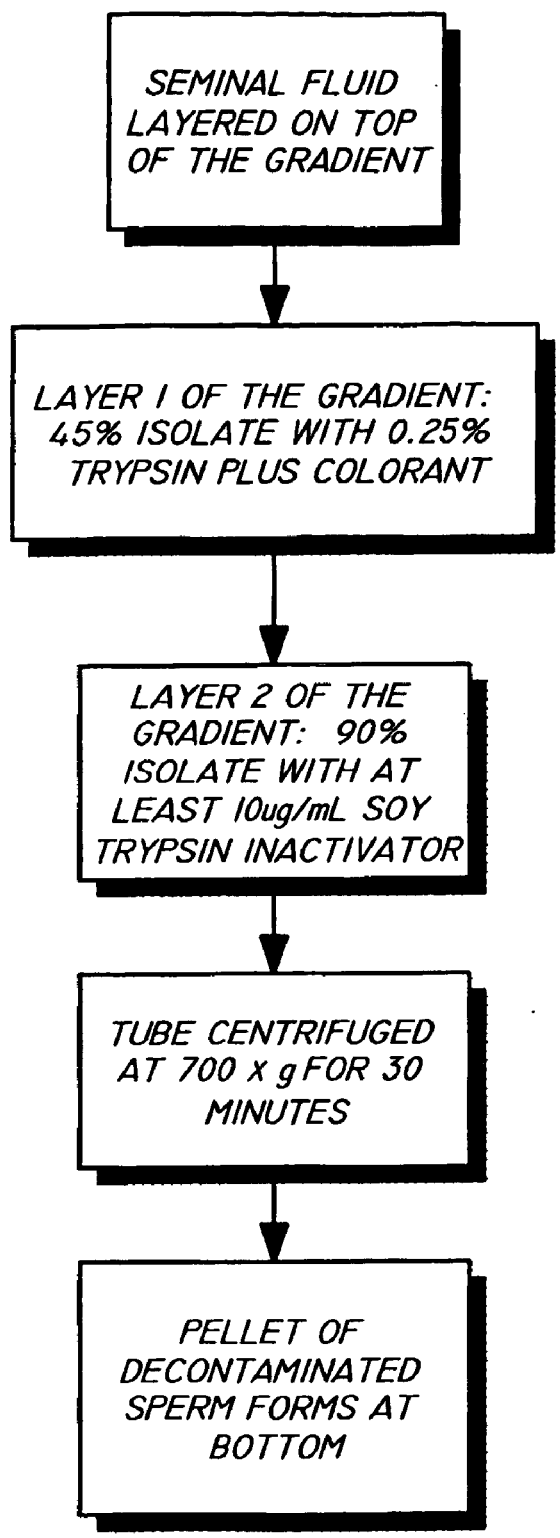
FIG. 6 is a flow diagram depicting an exemplary method of the present invention wherein a soy inactivator is utilized.

An exemplary embodiment of the virus decontamination process is shown in FIG. 5. Seminal fluid is layered on top of the gradient. The tube may be centrifuged which causes the seminal fluid to pass through both layers, resulting in the formation of a pellet of decontaminated sperm cells at the bottom. Centrifugation may occur at 700×g for 30 minutes or any suitable speed and time, as shown in FIG. 6. Although centrifugation is discussed, any process that will cause the seminal fluid to pass though the gradient layers may be used in accordance with the present invention.

FIG. 6 shows a more detailed exemplary embodiment of the virus decontamination process. The gradient is made of Isolate, however, a suitable preparation device such as Percoll, PureSperm, and the like may be used. The top layer of the gradient contains 1 ml of 45% Isolate containing 0.25% Trypsin or other suitable enzyme. This layer contains phenol red or some other colorant to show a visible difference from layer two. However, any or no colorant may be used. Under the 45% layer is 2 mL of 90% Isolate with at least 10 µg/mL Soy Trypsin Inactivator or other suitable inactivator. Soy inactivator is used because it will not introduce animal pathogens that may be present in animal by-product inactivators. 10 µg/ml may be the lowest effective concentration of inactivator to protect the sperm so at least that amount should be used. The amounts, percentages, and enzyme used may be changed according to the targeted virus or use.

Figure 7:
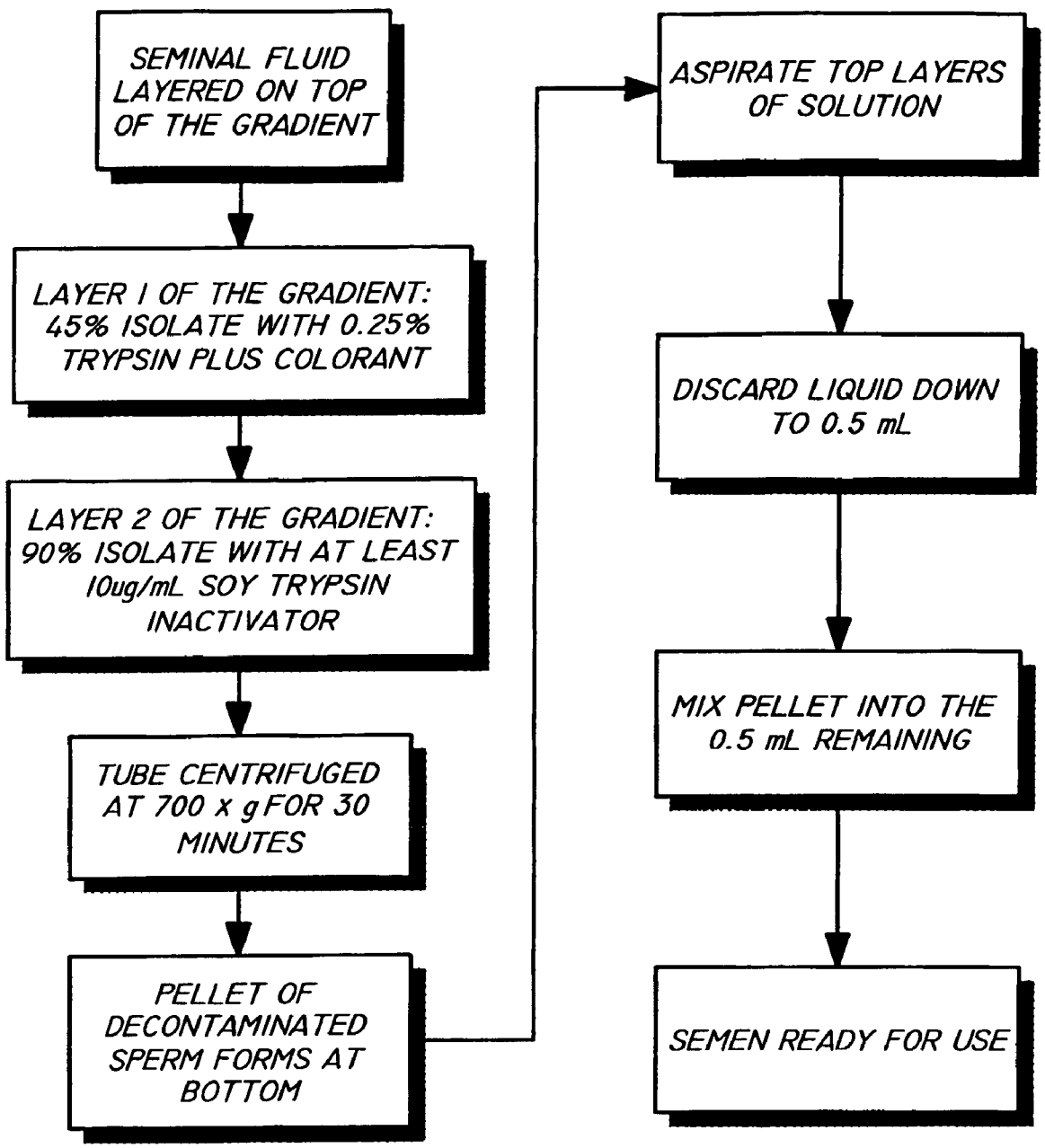
FIG. 7 is a flow diagram illustrating an exemplary method of the present invention wherein removal of a pellet is included.

FIG. 7 continues by showing that the solution is then aspirated. The top of the solution is discarded down to approximately 0.5 ml. The pellet is then gently and thoroughly mixed. The semen is now ready for use in applications such as artificial insemination, in-vitro fertilization, and other suitable applications as are known in the art.

Design of a Receptacle for the Isolate/Trypsin Treatment

Because of the technical skills necessary to properly perform Isolate density gradient centifugation (mostly in the layering, then aspiration of columns to ensure the layers are not mixed during the process), a design was suggested to facilitate this procedure for the final product. Although modeled after existing products, the suggested designs for this product would be different in that: (1) the plastic used for the semen "disinfection" procedure would be polystyrene, as opposed to polypropylene (which may leach toxic materials that can be detrimental to sperm when incubated for long periods at physiological temperature), and (2) the barrier used between the three components of the design may be made of a cell strainer, that would permit the free passage of sperm, yet provide some barrier to prevent excessive leakage of the Isolate gradients after centrifugation.

Thus, designs for this product may include a variety of differences from existing apparatus, for instance, the "filter" used in the semen "disinfection" procedure will not be a standard micropore filter, but rather, may employ loosely packed glass wool as an effective technique for washing diluted semen and removing damaged or non-viable sperm cells.

Change from PVP-Coated (Percoll) to Silane-Coated (Isolate) Silica Particles

An initial trial was conducted to compare sperm characteristics after application of the semen "disinfection" procedure using Percoll versus Isolate. The results are summarized in Table 1.

TABLE 1

Comparison of Percoll versus Isolate in semen "disinfection" procedure: domestic bull (*Bos taurus*) semen (1 ml) layered on top of 2 ml 45% (Percoll or Isolate) containing 0.25% trypsin over 2 ml 90% (Percoll or Isolate), centrifuged for 30 min at 700 × g then examined at 0 and 2 hours.

|  | % Motility | | Kinetic Rating[1] | | % Viability[2] | | % Acrosome Intact[2] | |
| --- | --- | --- | --- | --- | --- | --- | --- | --- |
|  | 0 h | 2 h | 0 h | 2 h | 0 h | 2 h | 0 h | 2 h |
| Initial (raw) | 43 | — | 3 | | 70 | — | 70 | — |
| Percoll | 60 | 50* | 2 | 2 | 90 | 41 | 93 | 43 |
| Isolate | 70 | 50 | 2 | 1.5 | 50 | 72 | 50 | 76 |

[1]Rate of forward progression (0 = no movement, to 5 fast, linear progression).
[2]As determined by vital staining (Eosin B/Fast Green).
*Sperm head agglutination observed.

Overall, Isolate appeared to result in lower percentages of damaged sperm (as reflected by the higher proportion of acrosome-reacted sperm and increased head agglutination observed in the Percoll group) but this was only observed after the 2 hour incubation (at room temperature) of the treated sperm in Percoll or Isolate.

Figure 8:
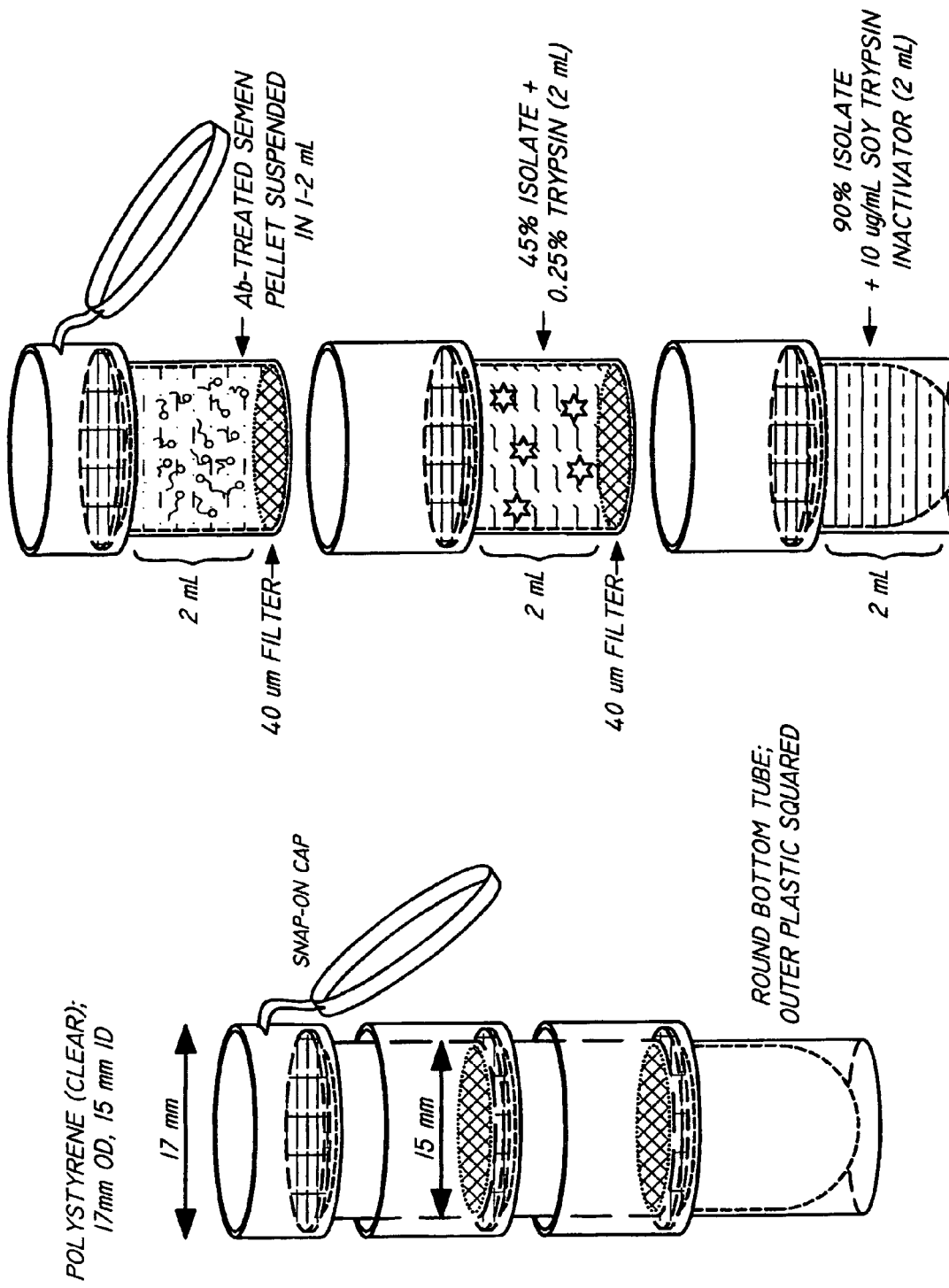
FIG. 8 is an illustration of an exemplary embodiment of the present invention wherein an apparatus suitable for enzyme treatment in accordance with the present invention is shown.

A detailed exemplary drawing of the decontamination apparatus is shown in FIG. 8. As stated earlier, the apparatus may be made of polystyrene and like materials so that no toxic chemicals leach into the solution inside. The measurements (volumes and sizes) listed in the drawing are estimated. Measurements may change due to amount of sample, use, or the like as desired by a person of ordinary skill in the art without departing from the spirit and scope of the present invention.

In FIG. 8, a more detailed description of the column, kit, or the like that may be used in the decontamination process. The left drawing shows an exemplary drawing of the apparatus itself. The right drawing shows the apparatus in an example usage. The drawing shows seminal fluid that has been previously treated with antibiotic. The virus treatment is not limited to this usage. The semen may be treated only for virus or only for bacteria without departing from the spirit and scope of the present invention.

The two layers may be contained in stacking type containers. The bottom container may have a squared outside and a round bottom tube inside. The squared outside may help with stability of the tube. Between each layer is a filter. The top container contains the semen solution. The second container will contain the 45% Isolate containing 0.25% enzyme and colorant. The bottom container will contain the 90% Isolate with 10 μg/ml soy enzyme inactivator. The entire apparatus will be centrifuged at 700×g for 30 minutes to form a pellet in the bottom container. The amount of solution, filter size, speed and time of centrifugation, sperm preparation device, and the like may be altered depending on the amount of sample, use, or the like.

Figure 9:
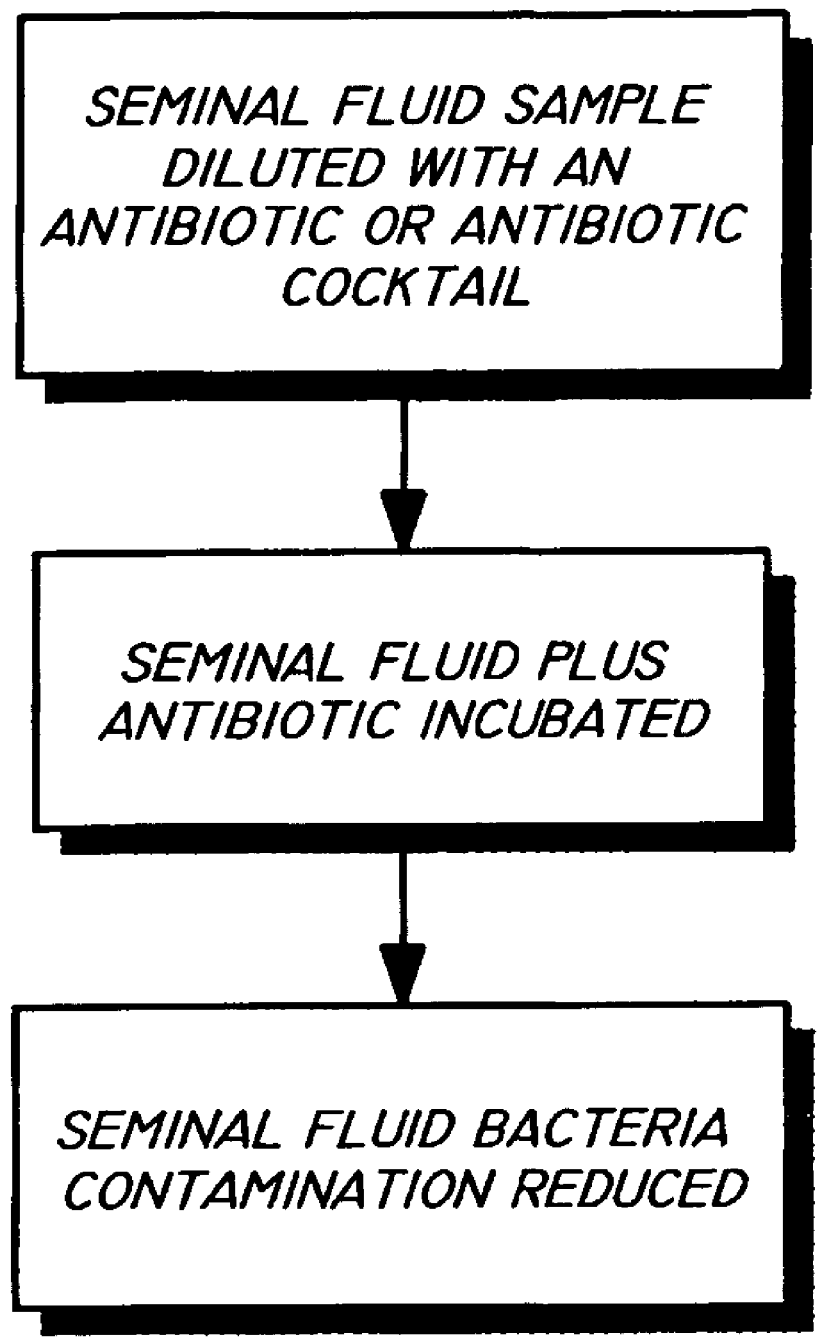
FIG. 9 is a flow diagram of an exemplary method of the present invention wherein antibiotic is also utilized.
Figure 10:
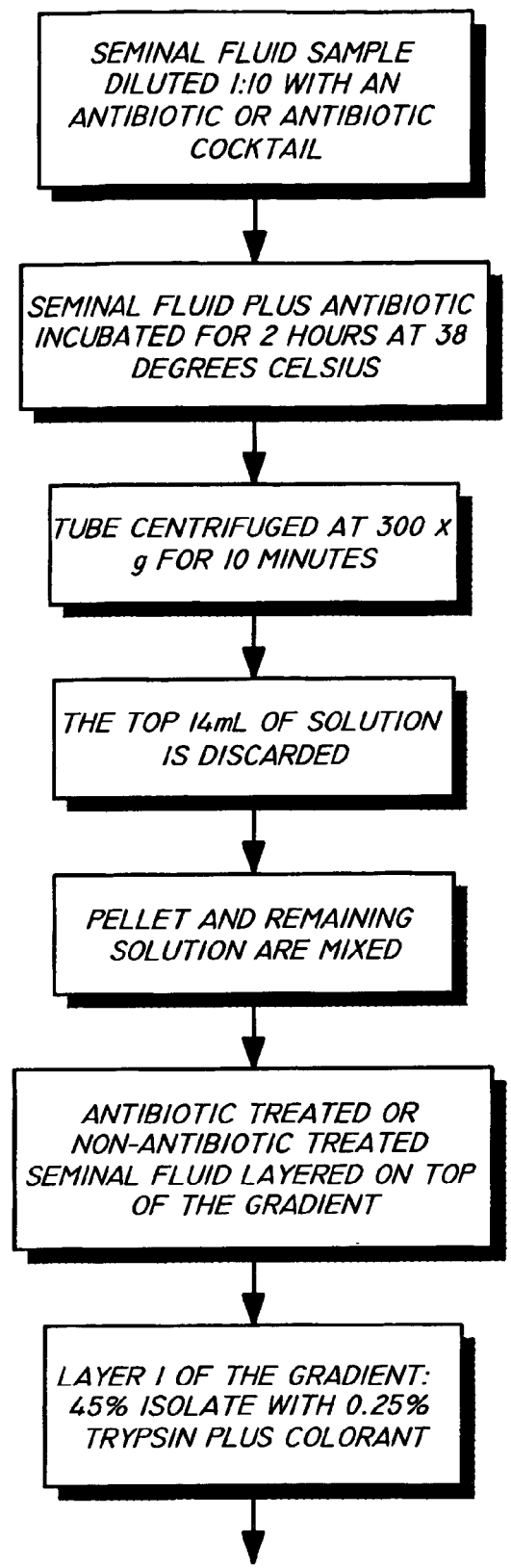
FIG. 10 is a flow diagram illustrating an exemplary method of the present invention wherein antibiotic and enzyme treatment is utilized.

FIG. 9 shows an exemplary embodiment of the process involving treatment to reduce bacteria. The treatment includes diluting seminal fluid with an antibiotic or antibiotic cocktail in a tube. Antibiotic is defined as anything that will inactivate bacteria as a pathogenic agent. The dilution of seminal fluid to antibiotic may be 1:10 (FIG. 10). This ratio may change depending on the virus, antibiotic used, and ultimate use of the seminal fluid. The cocktail may include one or more of the following: Gentamycin, Specinomycin, Lincomycin, Tylosin, Kanamycin, and any other appropriate antibiotic. By adding antibiotic, bacteria may be reduced or eliminated from seminal fluid. The seminal fluid plus antibiotic is incubated at physiological temperature for approximately 2 hours (FIG. 10). This incubation may be effective in reducing or eliminating bacteria contamination in the seminal fluid. The temperature and time may be altered depending on the bacteria and antibiotic used. In most cases, this process will eliminate any bacteria susceptible to the antibiotics applied. This process is effective and does not harm the sperm cell function. This process is beneficial as it may be used on both animal and human seminal fluid.

The tube described in FIG. 10 is centrifuged at approximately 300×g for 10 minutes to form a pellet in the bottom of the tube. The top 14 mL of the solution is discarded, leaving approximately 1 mL in the tube. The pellet and remaining solution are gently mixed. This 1 mL is layered on top of an isolate gradient in a conical tube. Speed and time of centrifugation, tube size or shape, and the amount of solution discarded and kept may be changed depending on the antibiotic or specific use for the sperm. Due to the application the sperm is used for, it may be desired that the sperm be more diluted requiring more solution left remaining.

Figure 11C:
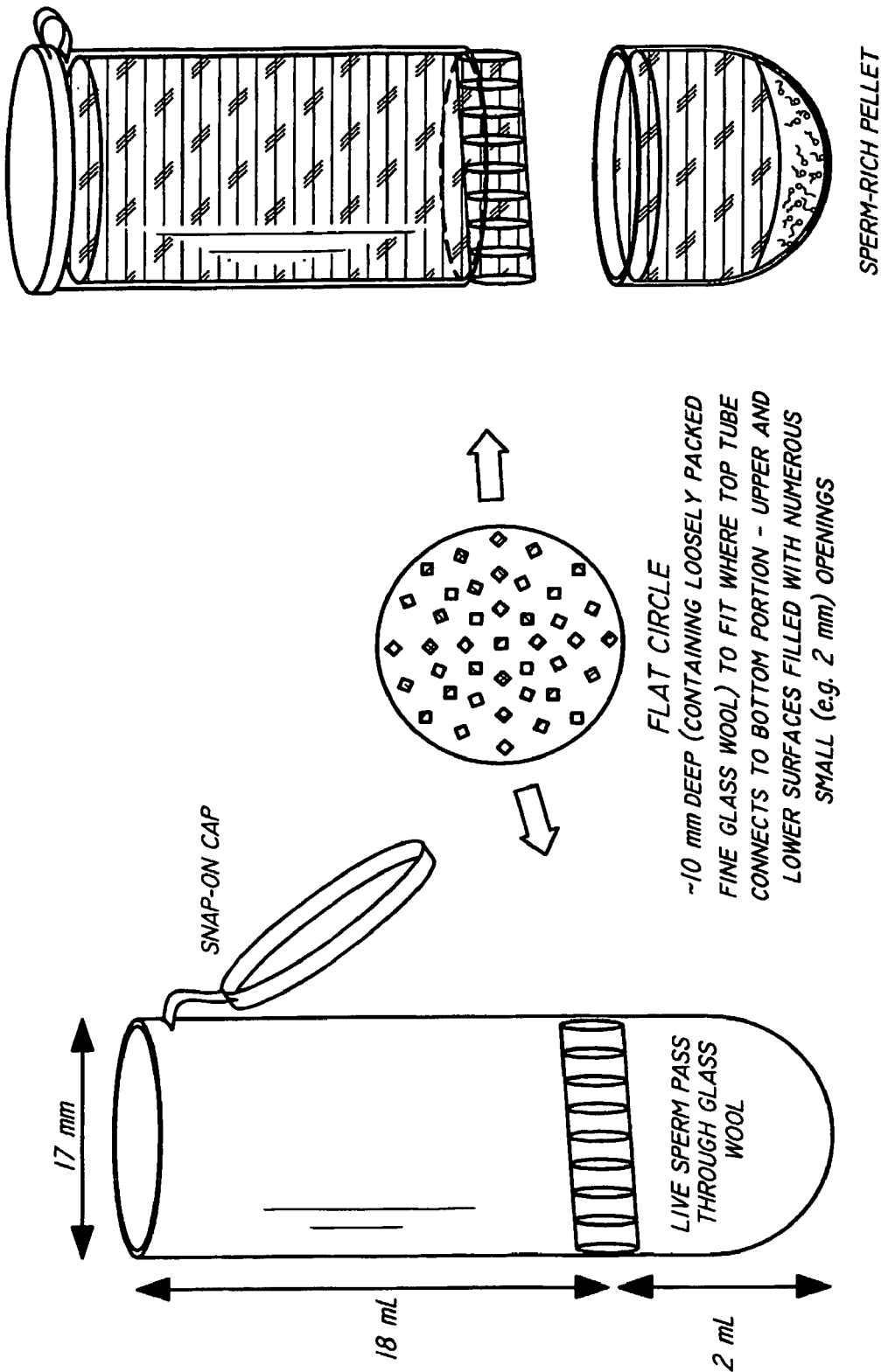
FIG. 11C is an illustration of an apparatus operable to embody the present invention in which an antibiotic cocktail treatment is shown.
Figure 13:
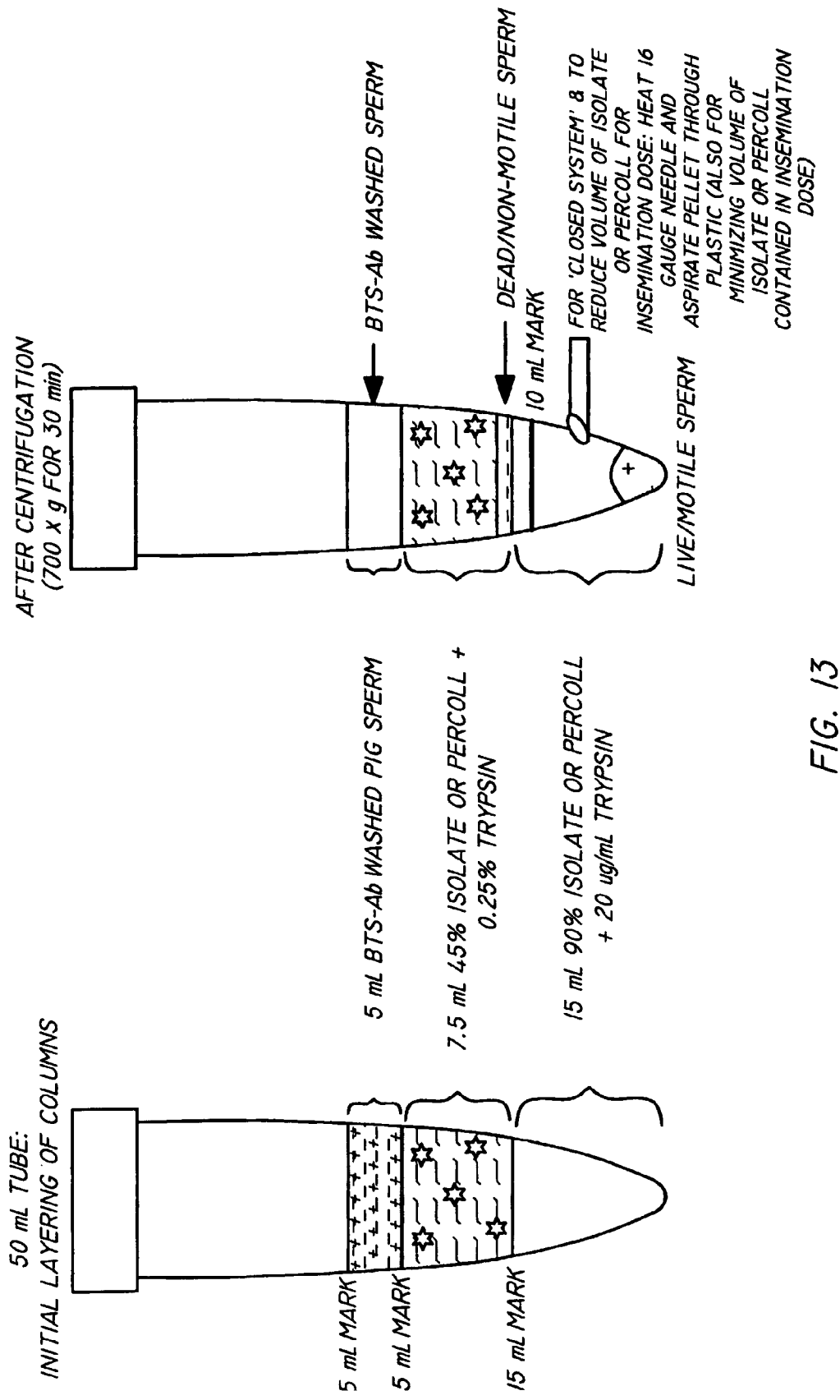
FIG. 13 is an illustration of an apparatus and method of an embodiment of the present invention in which a treatment for boar semen is shown.
Figure 14:
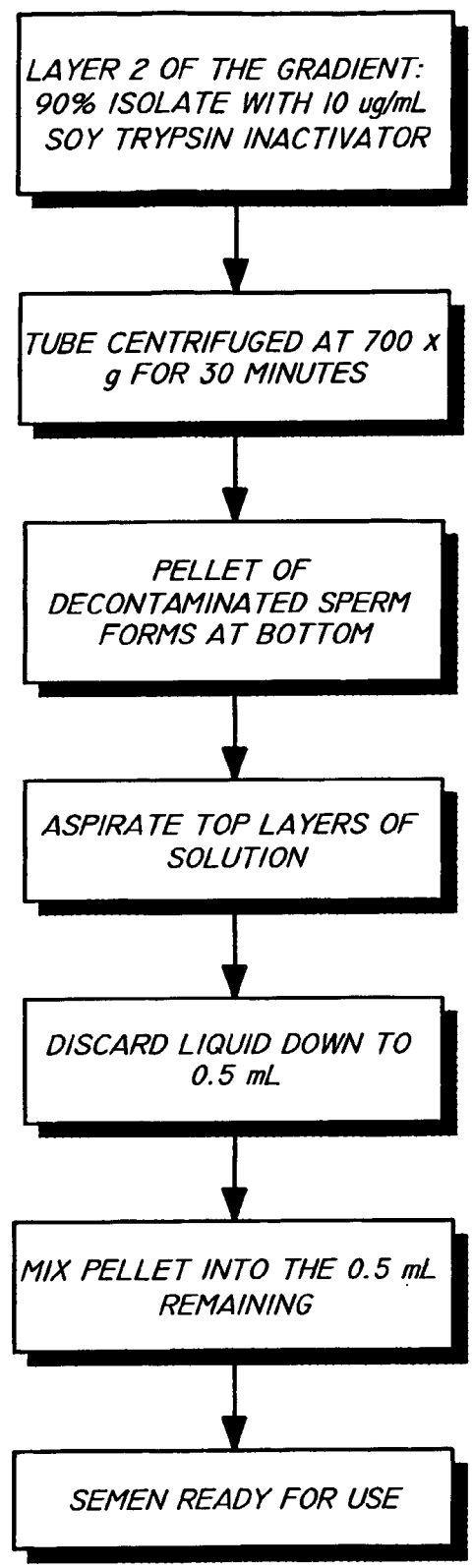
FIG. 14 is a flow diagram illustrating an exemplary method of the present invention.
Figure 20:
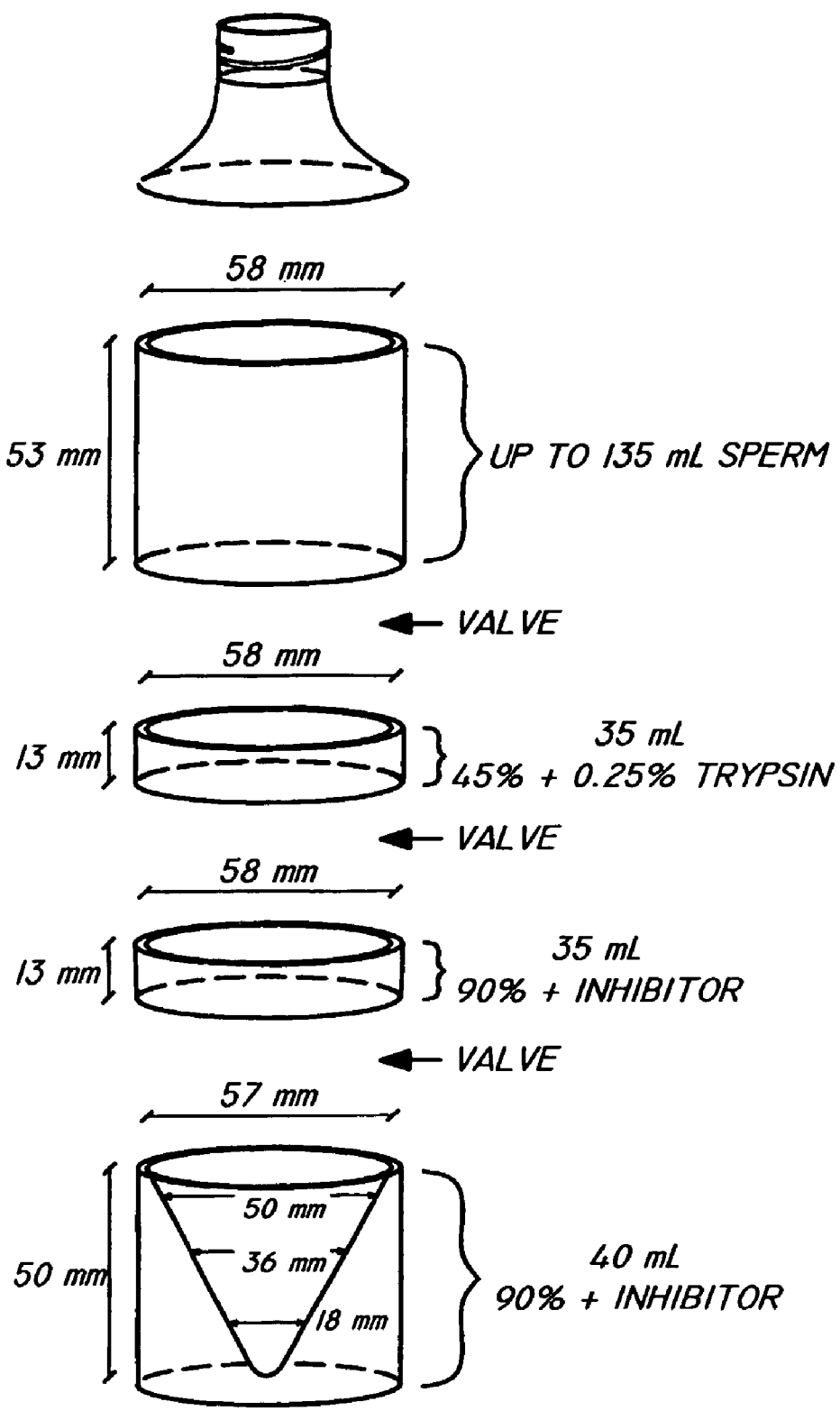
FIG. 20 is an illustration of an exemplary embodiment of the present invention wherein an apparatus for treatment of boar semen is shown.
Figure 21:
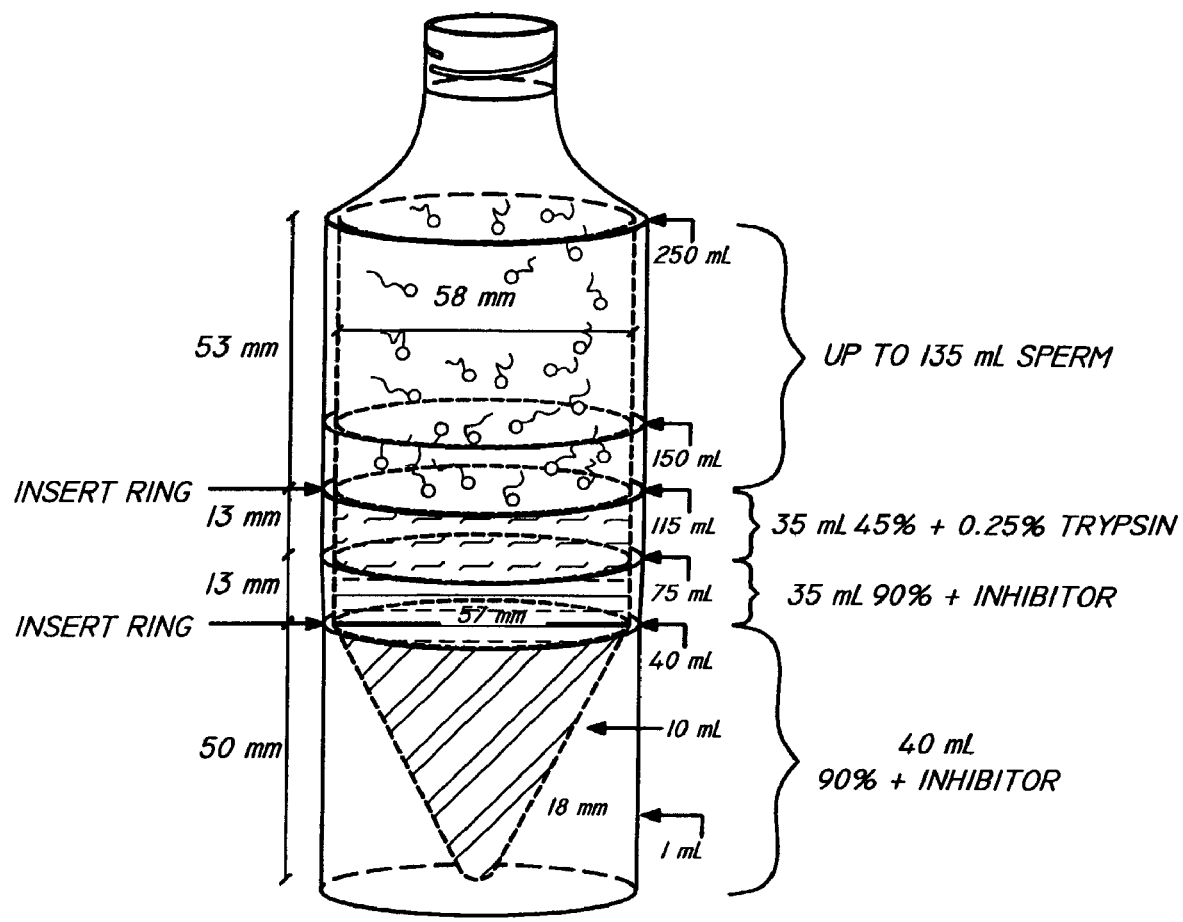
FIG. 21 is an illustration of an exemplary embodiment as shown in FIG. 20 wherein the apparatus is joined.
Figure 22:
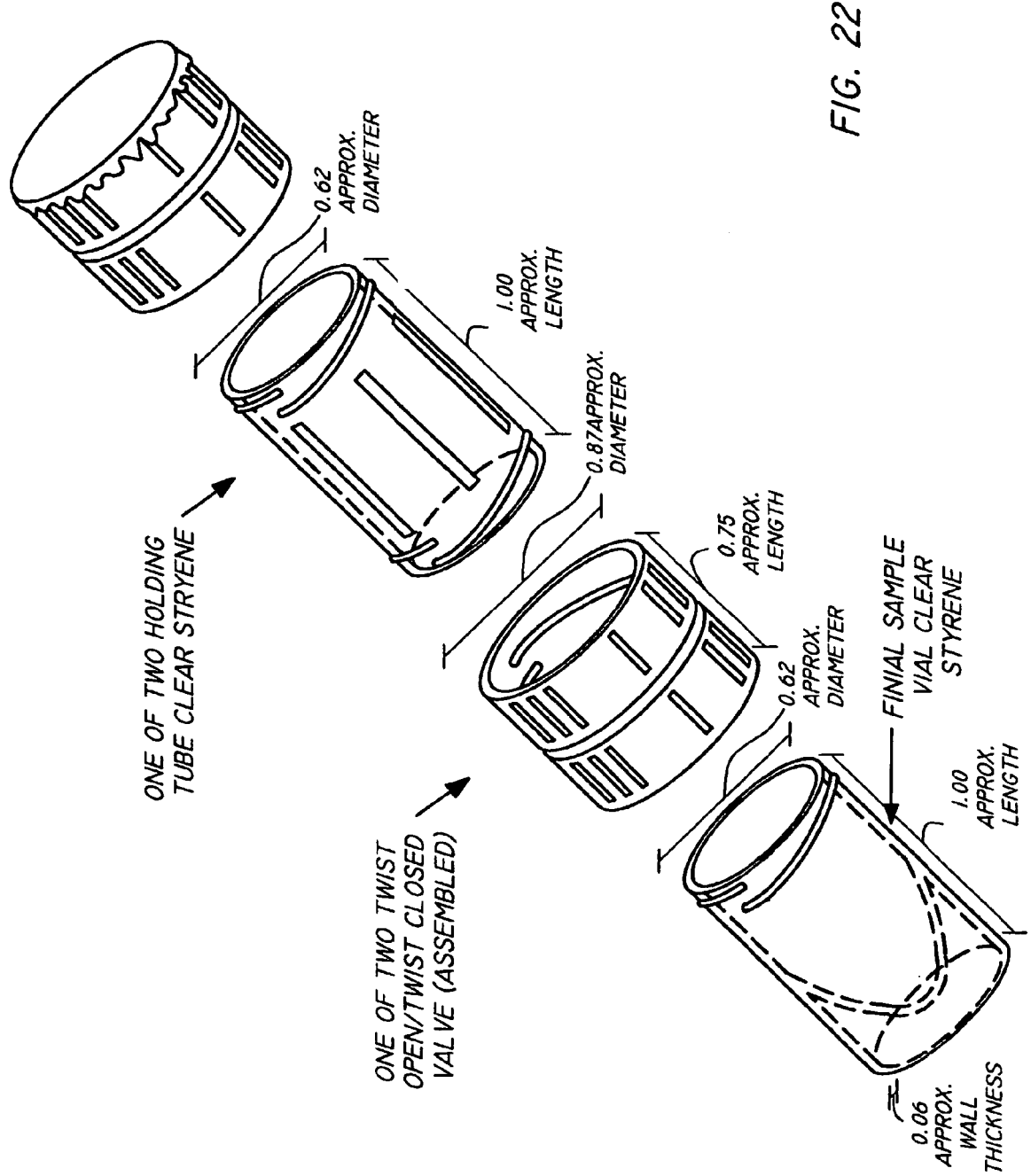
FIG. 22 is an illustration of an exemplary embodiment of the present invention wherein an apparatus including valves is shown.
Figure 23:
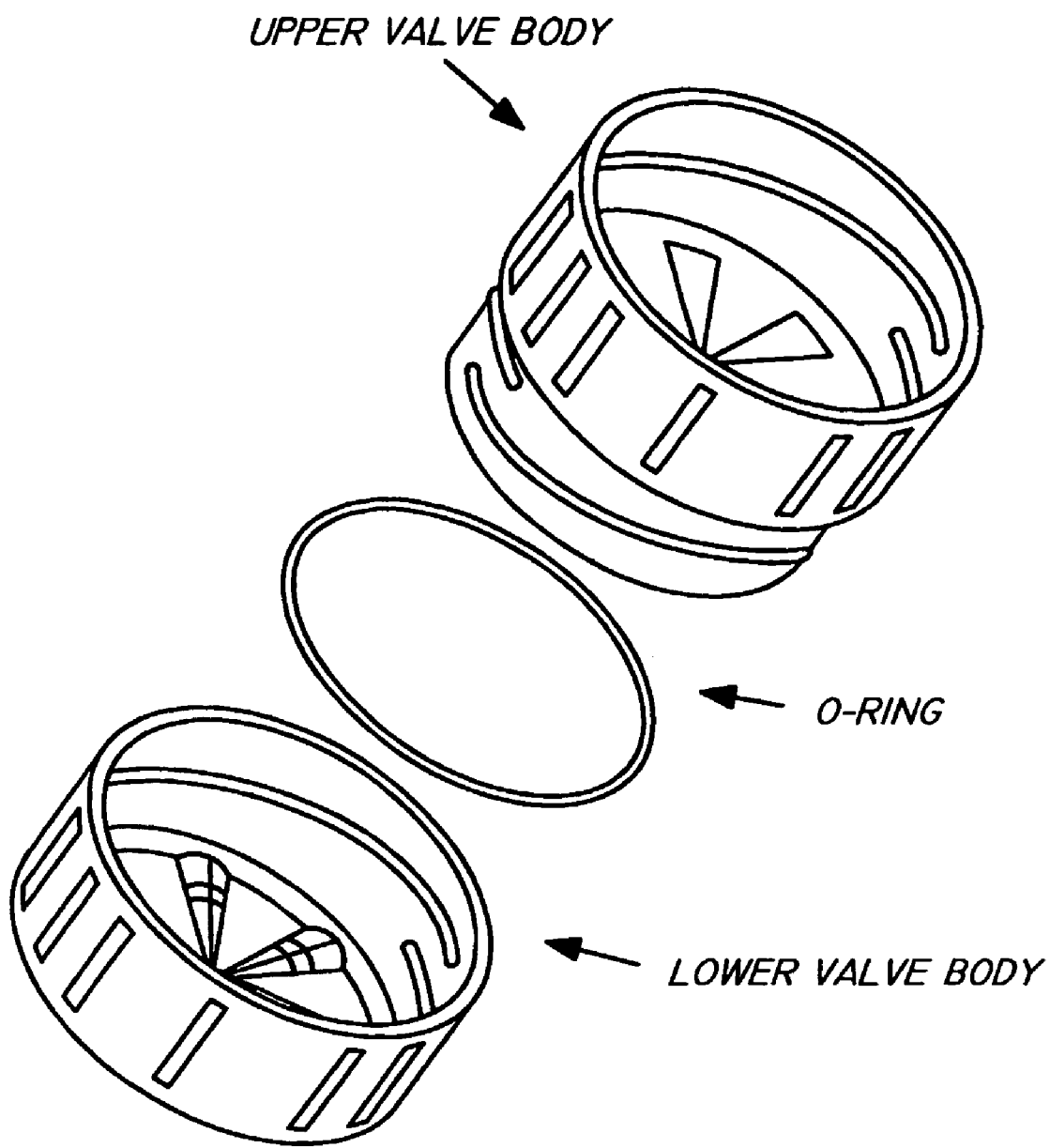
FIG. 23 is an illustration of an exemplary embodiment of the present invention wherein a valve of FIG. 22 is shown.

FIGS. 11 through 13 show various options for the antibiotic treatment apparatus. Each exemplary drawing consists of a two-part tube. Antibiotic diluted seminal fluid will be placed in the top portion. The bottom portion is the receptacle for the seminal fluid after it has passed though a glass wool layer. The glass wool section can take many forms, three of which are shown in the figures. Glass wool is used because it has been shown useful through experimentation in accordance with the present invention for removing damaged and/or non-viable sperm cells. There appears to be no products available that process semen of any species that use glass wool to achieve that purpose.

Experiments

A variety of experiments were employed to show the many advantages of the present invention and the unexpected benefits of providing "disinfection" of viruses and/or bacteria from biological samples, examples of which follow.

Sperm Survival after Treatment

In a first experiment, fresh semen was collected from six domestic bulls (*Bos taurus*) and from six gaur (*Bos gaur*) bulls and were treated in Percoll columns, with (positive control) or without (negative control) trypsin (0.125%) in a 45% column. As a result, there were no detrimental affects of the trypsin treatment as the sperm demonstrated no significant reduction in overall motility, no reduction in viability (as determined using vital staining), nor any significant damage in acrosomal integrity. Acrosomes are the caps on the sperm heads that contain enzymes that aid in penetrating the egg investments during fertilization. Release of these enzymes (termed acrosome reaction) is also associated with hyperactivation of the sperm (where they no longer are progressively motile, but rather, begin a 'figure eight' thrusting movement to add in penetrating the outer glyco protein shell (zona pellucida) surrounding the egg, or oocyte, which should occur only when in close proximity to the oocyte. Therefore, premature acrosome reactions or acrosome damage would limit the effectiveness of the sperm for standard artificial insemination procedures where sperm are deposited into the uterus.

Thus, the semen "disinfection" procedure was not detrimental to fresh (non-cryopreserved) bovine semen. It was important then to determine if the procedures worked equally well with cryopreserved semen, and if bovine sperm would survive treatment just prior to cryopreservation, which would be necessary if the procedure would be used to import bovine semen from other countries into the USA. A preliminary study was conducted using pooled semen collected from two domestic bulls (Bos taurus) to determine the spermatozoal viability if treated before or after cryopreservation.

The pooled bovine semen was divided into six treatment groups: (1) raw (no further processing); (2) raw, fresh, washed; (3) raw, fresh, treated; (4) treated then cryopreserved; (5) cryopreserved then treated; (6) cryopreserved only. The "washed" treatment incorporated medium without antibiotics and Percoll density gradient centrifugation without trypsin, and the "treated" groups used the antibiotic cocktail in the medium and 0.125% trypsin in the 45% Percoll layer. The results of this preliminary study are summarized in Table 2.

TABLE 2

Bovine sperm survival after semen "disinfection" treatment procedure (and control washes) before or after cryopreservation using a standard bovine method.

|  | % Motility | | | Kinetic Rating[1] | | % Viability[2] | | % Acrosome Intact[2] | | |
|---|---|---|---|---|---|---|---|---|---|---|
|  | 0 h | 2 h | 20 h | 0 h | 2 h | 0 h | 2 h | 0 h | 2 h | % IVF[3] |
| Raw (fresh) | 95 | 90 | 0 | 3 | 3 | 95 | 85 | 95 | 90 | NA |
| Fresh, wash | 100 | 80 | 40* | 3 | 4 | 84 | 78 | 83 | 78 | 80 (n = 15) |
| Fresh, treat | 100 | 90 | 60* | 4 | 3.5 | 78 | 82 | 79 | 75 | 66 (n = 18) |
| Treat, freeze | 60 | 20 | 0 | 3 | 2.5 | 64 | 44 | 56 | 43 | 62 (n = 8) |
| Freeze, treat | 80 | 60 | 20* | 3 | 3 | 50 | 65 | 66 | 50 | 53 (n = 17) |
| Freeze only | 80 | 50 | 10 | 4 | 3.5 | 72 | 60 | 72 | 65 | 60 (n = 15) |

[1]Rate of forward progression (0 = no movement, to 5 = fast, linear progression).
[2]As determined by vital staining (Eosin B/Fast Green).
[3]In vitro-matured bovine oocytes, 18 hours post-insemination (whole mount, acetoorcein); data reflects only monospermic (2 pronuclei) fertilization.
*Sperm head agglutination observed.

As a result of this preliminary trial, it appears that bovine sperm survives better if the semen "disinfection" procedure is applied after cryopreservation (and not before). However, because of the need to ensure that semen is treated before export, additional studies are needed to increase the viability of semen that are cryopreserved after treatment, however, it should be apparent that the present invention is successful in treatment before cryopreservation.

Efficacy of Procedure for Eliminating Specific Pathogenic Agents:

A. Treatment of Semen Inoculated with Known Pathogens

Although a great deal of research has been conducted in South Africa on developing successful protocols for cryopreserving sperm collected from hunted game species, none of the cryopreserved samples have ever been transported to the USA owing to USDA APHIS restrictions to the importation of tissues from animals in South Africa (and especially in Kruger National Park, which is regarded as endemic to viral diseases such as Foot-and-Mouth disease and rinderpest, which do not occur in North America). In light of the possible closure of the Poland quarantine station mentioned previously (and the devastating consequence this would have on any future importation of ungulates and suids from Africa and Asia into North America) as well as the bounty of potential genetic material that can be made available from game species hunted annually in South African National Parks (potentially for use in artificial insemination programs in North American zoos), a project was designed to test the efficacy of the semen "disinfection" method on ejaculated collected from free-ranging, African (Cape) buffalo (Syncerus caffer).

African buffalo were chosen as the animal model for this initial trial of the semen "disinfection" method for two initial reasons: (1) Kruger National Park was beginning a massive eradication program in 2000 to cull and hunt buffalo infected with tuberculosis (Mycobacterium bovis)—the goal was to capture and test 1,000 buffalo each year for five years (2000-2004), therefore, semen could be collected from animals known to have tuberculosis; and (2) African buffalo at Kruger National Park are known to be carriers of Foot-and-Mouth Virus, yet the African buffalo do not develop the clinical symptoms typical of the disease in domestic livestock (which can be economically devastating—as has recently been experienced by the Foot-and-Mouth Virus outbreak in Europe). The officials at Kruger National Park approved the proposal as realization of the great potential for the development of a semen "disinfection" method that may serve as a possible means for salvaging at least the genetic material from animals infected with tuberculosis before the animals are culled and hunted, as a long-term conservation strategy.

In light of the global interest in the Foot-and-Mouth Virus, the buffalo may also serve as a valuable model to test the effectiveness of the semen "disinfection" procedure on known, infected animals. A third objective was added to the Kruger National Park project, at the request of the park officials, to evaluate the effectiveness of the semen "disinfection" method on Brucellosis. A large percentage of the buffalo at Kruger National Park were also suspected, and later found, to be infected with Brucella abortus—another serious bacterial disease that causes spontaneous abortions in buffalo as well as domestic livestock.

Although the results of the preliminary experiments (described above) demonstrated that the semen "disinfection" procedures did not appear to be detrimental to sperm, it was equally important in the first phase of the buffalo investigation to determine if the procedure was also effective in removing the specific pathogens of interest (i.e., Mycobacterium bovis, Foot-and-Mouth Virus, and Brucella abortus).

To accomplish the goal of this initial phase, semen samples were collected from six African buffalo on a game ranch in South Africa, believed to be "disease-free" by the game manager. Those six samples were submitted to the Onderstepoort Veterinary Institute and each were divided into five aliquots, one aliquot of each raw semen sample was kept as the negative control, while the other four aliquots were individually inoculated with higher than physiological doses of the pathogens: (1) Brucella abortus, (2) Campylobacter species, (3) Mycobacterium bovis, and (4) Foot-and-Mouth Virus.

The raw semen and inoculated semen aliquots for all six buffalo were then processed in four treatment groups: 1) raw semen (negative control), 2) inoculated semen (positive control), 3) inoculated semen washed only (i.e., 2 hour incubation at 38° C. in medium without antibiotics, then Percoll density gradient centrifugation without trypsin) and 4) inoculated semen treated by 2 hour incubation at 38° C. in medium containing the antibiotic cocktail, then Percoll density gradient centrifugation using 0.125% trypsin in the 45% layer.

The final analyses for the presence of Brucella abortus, Campylobacter species and Foot-and-Mouth Virus has been completed and the results were similar for all three pathogen groups: 1) the non-inoculated raw semen (negative control) aliquots were all negative for the respective pathogens, 2) the inoculated raw semen (positive control) aliquots were all positive for the respective pathogens, 3) the washed only inoculated semen aliquots were mostly all positive (one of the six bull ejaculates inoculated with Campylobacter, and two of the ejaculates inoculated with Foot-and-Mouth Virus, were negative after simple washing), and 4) the inoculated raw semen aliquots treated with the antibiotic cocktail and trypsin were all negative.

The results of the Brucella abortus—inoculated semen samples indicate that the semen "disinfection" procedure was effective for eliminating two bacterial pathogens: Brucella abortus and Campylobacter species, and one viral pathogen: Foot-and-Mouth Virus, from buffalo semen samples that were experimentally inoculated with doses much higher than what would occur physiologically.

Efficacy of Procedure for Eliminating Specific Pathogenic Agents:

B. Treatment of Semen Collected from Infected Animals

The next phase of this study was to test the procedure on ejaculates collected from free-ranging buffalo at Kruger National Park known to be infected with Brucella abortus, Foot-and-Mouth Virus, and also Mycobacterium bovis. This investigation was actually initiated with semen samples collected from approximately 60 free-ranging buffalo. Those samples were aliquoted and subjected to three treatment groups: (1) raw semen, (2) washed semen (no antibiotics in the medium using for the 2 hour incubation and no enzymes added to the Percoll density gradient centrifugation), and (3) treated semen (2 hour incubation at 38° C. in the antibiotic cocktail followed by Percoll density centrifugation with trypsin in the 45% layer). All treated aliquots for each buffalo were then cryopreserved in liquid nitrogen where have been stored until the results were know from the phase one investigation (treatment of the buffalo semen inoculated with the different pathogenic agents).

After the first phase of experiments were conducted in South Africa and the results indicated that the semen "disinfection" procedure was effective in eliminating bacteria such as Brucella abortus and Campylobacter species from buffalo semen inoculated with those pathogenic agents, other antibiotics were explored to add to the original cocktail to increase the general effectiveness of the treatment for different microorganisms. However, there were two concerns in considering this modification of the existing protocol that utilized the CSS-approved antibiotic cocktail: (1) adding new antibiotics may attract the attention of veterinary regulatory agencies that are extremely sensitive to the overuse or abuse of novel antibiotics that may end up in food animals, and (2) certain antibiotics at specific concentrations can be detrimental to sperm.

The first concern is valid since it can be argued that the semen "disinfection" procedure can or will be used in the propagation of livestock by artificial insemination, so (theoretically) residual antibiotics may be injected into inseminated females via treated sperm. If this were the case, then resistant strains of bacteria may result in the inseminated females, which ultimately would negate the potential benefits of the novel antibiotic(s). Nevertheless, by design it is clear that the sperm processing procedure involving silane-coated, silica particle (Isolate, Irvine Scientific) density gradient centrifugation separates the viable sperm from the holding medium, whether that be seminal plasma or medium containing antibiotics, into the 90% column of Isolate.

The second concern is based on published reports of antibiotic efficacy and toxicity to sperm and other cell types. Riddeli and Stringellow (1998) provide a variety of antibiotics and ranges of concentrations that are tolerated in standard cell cultures and do not affect the in vitro development of murine embryos or bovine embryonic cell lines at a standard incubation temperature of 37° C. One antibiotic they tested, Kanamycin, showed very little toxicity to cultured cells and embryos even at relatively high concentrations (up to 1000 g/ml). Since Kanamycin is an accepted antibiotic supplement in commercial medium products used for embryo collection and transfer, the decision was made to add Kanamycin to the semen "disinfection" procedure at the maximal concentration of 1000 µg/ml. Tylosin is an antibiotic that is already included in the CSS-recommended antibiotic cocktail formulation at a concentration of 100 µg/ml and also at a minimal concentration of 200 µg/ml was for eliminating Mycoplasma species (a non-bacterial, non-viral pathogenic agent) from bovine embryos without detrimentally affecting embryonic development in vitro. For this reason, the Tylosin concentration in the semen "disinfection" procedure was increased to 200 µg/ml in the modified protocol.

To test the effect of the modified antibiotic cocktail on the viability of bovine sperm, a study was conducted. Semen was collected from three domestic bulls and after the initial analysis of semen characteristics, the semen was diluted 1:10 in the modified antibiotic cocktail, then incubated for 2 hours at 38° C. After incubation, the diluted semen was gently mixed and an aliquot removed for examination. The remaining volume was centrifuged at 300×g, to concentrate the treated sperm, then an aliquot was removed for examination as well as to inseminate a group of in vitro matured bovine oocytes. There were no significant increases in acrosome reactions at two hours post-treatment. The post-treatment estimations of progressive sperm motilities and fertilization of bovine oocytes by treated sperm are summarized in following table.

TABLE 3

Results of trial using modified antibiotic cocktail on fresh semen collected from each of three domestic bulls. Data is presented as overall percentage of sperm motility at 0, 2 and 22 hours or percentage sperm penetration (IVF) of bovine oocytes 18 hours post-insemination.

| | Raw | | Washed (prespin) | | | Washed | | Treated (prespin) | | | Treated | |
|---|---|---|---|---|---|---|---|---|---|---|---|---|
| | 0 h | 2 h | 0 h | 2 h | 22 h | 0 h | 2 h | 0 h | 2 h | 22 h | 0 h | 2 h |
| Bull1 | 95 | 90 | 90 | 90 | 40 | 90 | 90 | 90 | 80 | 20 | 90 | 80 |
| Bull2 | 95 | 95 | 90 | 90 | 60 | 90 | 90 | 90 | 80 | 15 | 90 | 80 |
| Bull3 | 90 | 85 | 90 | 90 | 0 | 80 | 80 | 90 | 90 | 10 | 80 | 80 |

Addition of Trypsin Inactivator to Prevent Enzyme Activity

One problem with the density gradient centrifugation technique for processing sperm is the potential problem for mixing layers during preparing or aspiration after centrifugation. If the 45% isolate layer containing active trypsin is inadvertently mixed with the final, 90% layer containing the sperm pellet, then the risk of prolonged exposure to enzymatic activity may indeed affect spermatozoal viability. One way to avoid this risk altogether is to add a trypsin inhibitor to the 90% layer. The inhibitor used is a soy-based product, therefore, there is no additional concern over possible pathogen contamination from an animal based product. In the initial trials with this product, using cryopreserved gaur (*Bos gaurus*) sperm, the recommended guidelines provided by Sigma Chemical Company (St. Louis, Mo.) were followed, which basically stated to use 1.4 mg of the inhibitor for every 1 mg of trypsin. However, it was clear that at this concentration, the thawed gaur sperm were not surviving beyond one hour post-exposure. A dose-response study was then performed (on the detachment of confluent somatic cell monolayers) to determine the minimal concentration of the soy-based inhibitor necessary to inactivate two concentrations of trypsin: 0.125% and 0.25%. As summarized in FIG. 15, the results indicated that the minimal concentration to achieve complete inactivation of trypsin was generally 10 μg/ml (which is almost 200 times less concentrated than that suggested by Sigma Chemical Co.).

A trial was then conducted using the inactivator at the lower concentration on fresh semen collected from each of three domestic bulls. When added to the 90% Isolate at 10 g/ml, the soy-based trypsin inactivator had no detrimental effect on bovine sperm motility, viability and acrosomal integrity, as summarized in Table 4A and 4B.

TABLE 4A

Effect of incubation of fresh bovine sperm in 90% Isolate without the addition of soy-based trypsin inactivator, and without trypsin in the 45% layer.

| | Raw | | Isolate without trypsin or inactivator 0 h | | | | Isolate without trypsin or inactivator 2 h | | | | Isolate without trypsin or inactivator 22 h | | | |
|---|---|---|---|---|---|---|---|---|---|---|---|---|---|---|
| | 0 h | 2 h | Mot | KR | Live | AI | Mot | KR | Live | AI | Mot | KR | Live | AI |
| Bull 1 | 95 | 90 | 80 | 3 | 78 | 79 | 90 | 4 | 91 | 92 | 20 | 3 | — | — |
| Bull 2 | 95 | 95 | 80 | 3 | 77 | 82 | 90 | 4 | 75 | 87 | 10 | 2 | — | — |
| Bull 3 | 90 | 85 | 80 | 3 | 77 | 88 | 60 | 3 | 82 | 82 | 10 | 3 | — | — |

Key:
Mot = overall % motility;
KR = kinetic rating (0 = no movement to 5 = fast, linear movement;
Live = % viable by vital staining;
AI = % acrosome intact.

TABLE 4B

Effect of incubation of fresh bovine sperm in 90% Isolate, with the addition of 10 g/ml soy-based trypsin inactivator, and with 0.25% trypsin in the 45% layer.

| | Raw | | Isolate with trypsin + inactivator 0 h | | | | Isolate with trypsin + inactivator 2 h | | | | Isolate with trypsin + inactivator 22 h | | | |
|---|---|---|---|---|---|---|---|---|---|---|---|---|---|---|
| | 0 h | 2 h | Mot | KR | Live | AI | Mot | KR | Live | AI | Mot | KR | Live | AI |
| Bull 1 | 95 | 90 | 80 | 3 | 84 | 85 | 60 | 3 | 78 | 82 | 10 | 1 | — | — |
| Bull 2 | 95 | 95 | 80 | 3 | 76 | 78 | 60 | 3 | 84 | 85 | 10 | 2.5 | — | — |
| Bull 3 | 90 | 85 | 80 | 4 | 72 | 72 | 80 | 3 | 73 | 84 | 0 | 0 | — | — |

Key:
Mot = overall % motility;
KR = kinetic rating (0 = no movement to 5 = fast, linear movement;
Live = % viable by vital staining;
AI = % acrosome intact.

As a result, there were no significant differences between the three bull sperm populations that were treated with Isolate gradient centrifugation without trypsin and the soy-based trypsin inhibitor, or with 0.25% trypsin in the 45% layer and 10 μg/ml soy-based trypsin inactivator in the 90% layer. Because of the benefits of using this enzyme inhibitor, the semen "disinfection" procedure was modified to include this product in an embodiment of the present invention.

Preliminary Trials on Boar Semen

In light of the preference for the BTS medium for boar semen, an preliminary study was first performed on the pooled semen to determine if BTS was more optimal than the TL Hepes Solution (used in the semen "disinfection" procedure) for use with swine. A 1:5 dilution (semen: medium) was made using: 1) TL Hepes Solution, 2) TL Hepes Solution containing the modified antibiotic cocktail, 3) BTS medium (which does not contain bovine serum albumin nor phenol red), and 4) BTS medium containing the modified antibiotic cocktail. The four treatments were then incubated at 39° C. (physiological temperature for pigs) and then the diluted sperm was concentrated by centrifugation at 300×g for 10 min and evaluated. The results are summarized in Table 5.

TABLE 5

Initial trial incubating 10 ml pooled boar semen (0.648 × $10^9$/ml) in two different media, with and without the supplementation of antibiotic cocktail, then centrifuged for 10 min at 300 × g and examining sperm characteristics, aspirating and discarding supernatant and reconstituting the sperm-rich pellet in 5 ml remaining medium (Note: final sperm concentrations in the washed 5 ml are essentially similar to starting concentration in 10 ml).

| | Sperm | | Acrosomal Integrity* | | | |
|---|---|---|---|---|---|---|
| | Conc × $10^9$/ml* | % Prog Motile | % Normal | % Damaged | % Missing | % Loose |
| TL Hepes | — | 85 | — | — | — | — |
| TL Hepes + Ab | 1.233 | 85 | 97 | 0 | 2 | 1 |
| BTS | — | 90 | — | — | — | — |
| BTS + Ab | 1.186 | 90 | 96 | 1 | 2 | 1 |

*Only performed on those treated in the presence of the antibiotic (Ab) cocktail.

Essentially there was no immediate difference with the IL Hepes Solution versus the BTS medium for incubating boar sperm with or without the supplementation of the antibiotic cocktail. The 5 ml washed sperm concentrate from both medium groups was then placed on a modified Isolate density gradient column, the design was made after a preliminary trial using the standard 2 ml columns of 45% and 90% in a 15 ml conical tube was found not to provide enough volume necessary to separate the large concentration of viable boar sperm in the pooled ejaculate, and that would be needed for a standard insemination dose of approximately 5×$10^9$ sperm—diluted in a total volume of 100 ml (semen with or without extender).

The results of the boar sperm characteristics of aliquots incubated initially in either the IL Hepes Solution—or—the BTS medium supplemented with the antibiotic cocktail, then concentrated to 5 ml by centrifugation at 300×g for 10 min and processed through the isolate density gradient centrifugation (700×g for 30 min) are summarized in Table 6 (Note: the sperm pellet was reconstituted in the approximately 10 ml of 90% Isolate containing 20 μg/ml soy-based trypsin inactivator) and incubated at room temperature):

TABLE 6

Boar sperm characteristics after the antibiotic treatment - cocktail supplemented to either TL Hepes Solution or BTS medium; Note: TL Hepes contains 3 mg/ml BSA, BTS contains no protein) then Isolate gradient centrifugation using 0.25% trypsin in the 45% layer. The sperm pellet was reconstituted in the remaining 10 ml of Isolate and incubated at room temperature (on the bench top) for the periods indicated.

| | Hours incubation | Sperm Conc × $10^9$/ml* | % Motility | Acrosomal Integrity* | | | |
|---|---|---|---|---|---|---|---|
| | | | | % Normal | % Damaged | % Missing | % Loose |
| TL Hepes | 0 (3 pm) | 1.2 | 55 Progressive | 94 | 1 | 3 | 2 |
| | 5 (8 pm) | — | 60 Progressive | 98 | 0 | 2 | 0 |
| | 17 (8 am) | — | 20 Non-Progress | — | — | — | — |
| BTS | 0 (3 pm) | 0.97 | 80 Progressive | 97 | 1 | 0 | 2 |
| | 5 (8 pm) | — | 60 Progressive | 94 | 0 | 6 | 0 |
| | 18 (8 am) | — | 10 (Half Progress) | — | — | — | — |

*Concentration of pooled raw semen (before dilution) = 0.648 × $10^9$/ml; Concentration after 2 h incubation with Ab then concentration (300 × g, 10 min) to 5 ml: TL Hepes: 1.233 × $10^9$/ml and BTS: 1.186 × $10^9$/ml.

Domestic Cattle

A second trial was conducted on domestic bull semen. A total of 10 samples were provided and the semen disinfection procedure was performed blindly without knowing which of the samples contained pathogens. In the group of 10 semen samples, two samples came from bulls persistently infected with bovine viral diarrhea (BVD) virus, four samples from bulls acutely infected with BVD virus, and two samples from healthy bulls served as the negative controls.

After treatment the samples were assayed by using two procedures: virus isolation that detects active virus (cytotoxic effects) and polymerase chain reaction which detects any presence of the viral particles even if the virus had been inactivated. The results were as follows:

| Sample # | Virus used | virus isolation | PCR |
|---|---|---|---|
| 1 | BVDV-persistent | Looks + ?? | +/+ |
| 2 | BVDV-persistent | looks Neg ?? | neg |
| 3 | BVDV-acute | looks Neg ?? | neg |
| 4 | BVDV-acute | looks + ?? | neg |
| 5 | BVDV-acute | looks Neg ?? | neg/+ |
| 6 | BVDV-acute | looks Neg ?? | +/neg |
| 7 | Neg control | neg | neg |
| 8 | Neg control | neg | neg |

In conclusion, some of the samples containing active virus, especially those from the bulls acutely infected with BVD, were cleared of the virus. Some of the other samples from acutely or persistently infected animals tested positive.

A study was conducted to test the semen disinfection procedure on domestic bull semen samples inoculated with *Brucella abortus* and *Campylobacter* spp. bacteria. A total of 21 cryopreserved semen samples from several economically important, indigenous breeds of cattle were spiked with the bacteria then processed using the semen disinfection procedure. Each sample was divided into four aliquots: (1) non-inoculated (negative) control, (2) inoculated (positive)

control, (3) inoculated —washed (in medium only and centrifuged in Percoll density gradients without added trypsin, and (4) inoculated—treated (in medium containing the antibiotic cocktail and centrifuged in Percoll density gradients containing trypsin). The treated sperm resulting from all four treatments for the semen samples from each of the 21 bulls were then streaked onto agar plates and incubated for 3-5 days for bacterial growth. The 21 "treated" samples (treatment 4 above) were also submitted for antibiotic residue analysis (gentamycin, spectinomycin, lincomycin, tylosin and kanamycin). This last step was important to prove that there would be no residual antibiotics present in the treated sperm sample that can be transferred to a recipient cow during an artificial insemination procedure. The results of the antibiotic residue analysis have not yet been received. The results from the bacterial cultures for the four treatments are shown as follows:

Bacterial Culture of the Semen of Indigenous African Cattle Breeds

Bacterial cultures provided: *Brucella abortus* Strain 19 [vaccine strain]—suspension at $10^8$ per ml. *Campylobacter fetus*—recent laboratory isolate [4914] from a bull in an infected herd in the Kuruman district—suspension at $10^7$/ml. 0,1 ml of each suspension was added to the semen samples, ie both *Brucella* and *Campylobacter* were added to one tube of semen. Both isolates were sensitive to several of the antibiotics used in the novel disinfection procedure. *B. abortus* was sensitive to gentamicin, kanamycin and spectinomycin, intermediate to tylosin and resistant to lincomycin. *C. fetus* was sensitive to gentamicin, kanamycin and lincomycin, and intermediate to tylosin and spectinomycin.

At the end of the procedure, all 84 samples of 21 semen, marked N, P, W and T were cultured on duplicate blood tryptose agar plates, prepared with bovine blood by Onderstepoort Biological Products.

One of each plate was incubated in 5% $CO_2$ in air, and the other in an anaerobic pot containing gas generating sachets [Oxoid, BR 56/60]

The results of culture were as follows:

| Sample no. | N | P | W | T |
|---|---|---|---|---|
| 1 | N | C & B | B | N |
| 2 | N | B | N | N |
| 3 | N | B | N | N |
| 4 | N | N | N | N |
| 5 | N | B | B | N |
| 6 | N | B | N | N |
| 7 | N | C & B | N | N |
| 8 | N | C & B | N | N |
| 9 | N | B | N | N |
| 10 | N | C & B | N | N |
| 11 | N | C & B | N | N |
| 12 | N | N | B* | N |
| 13 | N | B | B | N |
| 14 | N | B | B | N |
| 15 | N | C & B | N | N |
| 16 | N | C & B | N | N |
| 17 | N | C & B | N | N |
| 18 | N | C & B | N | N |
| 19 | N | C & B | N | N |
| 20 | N | N | N | N |
| 21 | N | C & B | N | N |

Headers N, P, W and T—as in protocol
In table—N = negative; C = growth of *C. fetus*; B = growth of *Brucella*
*= only one colony isolated The *C. fetus* isolate must have been much more sensitive to the effects of the antibiotics used, as the levels of isolation were much lower throughout.

Conclusions: The semen disinfection procedure was successful in eliminating the two species of bacteria from bull semen inoculated with the organisms. An interesting outcome of this experiment was that simply "washing" the sperm in medium without antibiotics and centrifuging through the Percoll layers without trypsin was completely effective for eliminating *Campylobacter* spp., but not totally effective for removing *Brucella abortus* (5 of the 21 washed samples contained the bacteria). Another interesting and unexpected outcome was in the inoculated (positive) controls: 3 tested negative, and 7 of the 21 tested negative for *Campylobacter* spp., but positive for *Brucella abortus*. This can be explained by that fact that we were using cryopreserved semen which is typically frozen using diluents that contain antibiotics. That being the case, all of the 21 samples should have shown negative results as the antibiotics in the cryodiluents should have killed the bacteria that was placed into the diluted semen sample, that was incubated at room temperature for approximately four hours before streaking onto agar (during which the washing and treatment procedures were being performed). What this means is either the antibiotics in the cryopreserved semen samples had degraded or lost activity, or that the amount of bacteria that was placed into the sample overwhelmed the amount of antibiotics present.

Poultry

A trial was conducted on rooster and turkey semen. Research has found that the bacteria *Salmonella* spp. and *Campylobacter* spp., which are problematic in poultry production, can be transmitted sexually to the egg yolk from the semen of infected males. At the time of the trial, testing was being performed of several new commercial media containing novel antibiotic preparations and found that none of those (at that time) were completely effective for removing *Salmonella* spp. In subsequent trials using the antibiotic cocktail in the present semen disinfection technique, complete elimination of both *Campylobacter* spp. and *Salmonella* spp was achieved.

Swine

Semen was collected from a total of 18 boars from a stud that recently had an outbreak of the porcine reproductive and respiratory syndrome (PRRS) virus. The semen was extended in a boar semen diluent and transported overnight and the semen disinfection procedure of the present invention performed. Samples of the 18 untreated and treated samples were then sent for PCR analysis. Four of the 18 untreated samples were reported as "suspect" for the PRRS virus, whereas all of the 18 treated samples were negative.

Owing to the current level of concern by boar producers regarding the PRRS virus outbreak, efforts are specifically being made on reducing the costs of the procedure by treating whole ejaculates before they are divided into artificial insemination doses and transported to farms.

One of the major developments in making the semen disinfection procedure easier to perform is the design of a unique tube that will greatly facilitate the layering of the Percoll gradients. An exemplary design is shown in FIGS. 18, 19, 20, 21, 22 & 23.

Additional studies are planned and in progress using the method of the present invention, including the following:
1. Foot-and-mouth disease virus and brucellosis in African buffalo (Appendix 2).
2. Foot-and-mouth disease virus, rift valley fever virus and enzootic bovine leucosis virus in indigenous African cattle breeds: Bonsmara, Nguni and Boran (Appendix 3).

3. Lumpy skin disease virus and heartwater in indigenous African cattle breeds: Bonsmara, Nguni and Boran (Appendix 4).
4. HIV, Hepatitis B and C in humans (Appendix 5).

In an embodiment of the present invention, the apparatus is designed to process an entire ejaculate. The raw sample is initially centrifuged (300×g for 10 min) to reduce the volume and increase the sperm concentration. The concentrated sperm is transferred to the semen disinfection tube for treatment. A maximum volume of 135 ml of concentrated sperm can be processed per tube.

Costs of Processing an Entire Ejaculate

| MEDIA | | | |
|---|---|---|---|
| 90% PERCOLL | $.30/ml × | 91.75 ml = | $27.53 |
| TYRODES | $.04/ml × | 13.125 ml = | $.47 |
| TRYPSIN | $.18/ml × | 9.375 ml = | $.76 |
| TRYPSIN INHIBITOR | $.49/ml × | .750 ml = | $.37 |
| TUBE | $.12 × | 1 = | $.12 |
| TECHNICIAN | $9.35 × | .75 (45 min.) = | $7.00 |
| | | TOTAL = | $36.25 |

Costs Based on Artificial Insemination (AI) Dose

EXAMPLES

1. This is an actual example taken from a recent boar collection by Dr. Brett White, University of Nebraska at Lincoln).

| | |
|---|---|
| Raw Concentration: | $287 \times 10^6$/ml |
| Raw Volume: | 500 ml |
| Number of Sperm in Entire Sample: | 143.68 billion |

| Billion of Sperm/AI | Number of AI Doses* | Cost Per AI Dose |
|---|---|---|
| 5 | 28.74 | $1.26 |
| 4 | 35.92 | $1.01 |
| 3 | 47.89 | $.76 |
| 2 | 71.84 | $.50 |
| 1 | 143.68 | $.25 |

2. This is an example based on an average collection at Sygen Intl. (information provided by Jeff Altfillisch)

| | |
|---|---|
| Raw Concentration: | $300 \times 10^6$ |
| Raw Volume: | 250 |
| Number of Sperm in Entire Sample: | 75 billion |

| Billion of Sperm/AI | Number of AI Doses* | Cost Per AI Dose |
|---|---|---|
| 5 | 15 | $2.42 |
| 4 | 18.75 | $1.93 |
| 3 | 25 | $1.45 |
| 2 | 37.5 | $.97 |
| 1 | 75 | $.48 |

*AI doses using raw (non-treated) ejaculates typically range from 3-5 billion sperm dose without adjusting for the percentages of live or motile sperm. The concentrated sperm treated with the semen disinfection procedure will be close to 100% motile (as only motile sperm can pass through the density gradients). It is, therefore, highly probable that the total numbers of sperm used per AI dose can be reduced significantly, thereby reducing the cost of the semen disinfection procedure per AI dose.

In exemplary embodiments, the methods disclosed may be implemented as sets of instructions or software readable by a device. Further, it is understood that the specific order or hierarchy of steps in the methods disclosed are examples of exemplary approaches. Based upon design preferences, it is understood that the specific order or hierarchy of steps in the method can be rearranged while remaining within the scope of the present invention. The accompanying method claims present elements of the various steps in a sample order, and are not meant to be limited to the specific order or hierarchy presented.

It is believed that the method and apparatus of the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof. It is the intention of the following claims to encompass and include such changes.

What is claimed is:

1. A method for reducing pathogens in a biological sample, comprising:

passing the biological sample through a gradient, the gradient including an enzyme layer, the enzyme layer including an enzyme suitable for at least one of enzymatically-inactivating and enzymatically-degrading at least one pathogen included in the sample;

passing the biological sample through an enzyme inactivator layer suitable for inactivating the enzyme, wherein the biological sample includes sperm and the at least one pathogen includes at least one of a virus and bacteria.

2. The method as described in claim 1, wherein the enzyme inactivation layer includes an inactivator in a concentration of at least one of approximately 10 μg/ml and below 20 μg/ml.

3. The method as described in claim 1, wherein the enzyme is a proteolytic enzyme.

4. The method as described in claim 3, wherein the enzyme includes trypsin and has a concentration of generally approximately 0.125%.

5. The method as described in claim 3, wherein the enzyme includes trypsin and has a concentration of approximately 0.25% and below.

6. The method as described in claim 1, wherein passing includes centrifuging the gradient and the biological sample.

7. The method as described in claim 1, further comprising passing the biological sample through a filter.

8. The method as described in claim 7, wherein the filter is suitable for substantially hindering passage of at least one of nonmotile and damaged sperm including in the biological sample.

9. The method as described in claim 1, wherein the pathogen includes at least one of foot-and mouth virus, HIV, Hepatitis, tuberculosis, brucellosis, brucella abortus, mycobacterium bovis, mycoplasma species, porcine reproductive and respiratory syndrome virus and bovine viral diarrhea virus.

10. The method as described in claim 1, further comprising diluting the biological sample with an antibiotic.

11. A method for reducing pathogens in a biological sample, comprising:

treating the biological sample with an antibiotic; and passing the biological sample through a gradient, the gradient including an enzyme layer, the enzyme layer including an enzyme suitable for at least one of enzymatically-inactivating and enzymatically-degrading at least one pathogen included in the sample;

passing the biological sample through an enzyme inactivator layer suitable for inactivating the enzyme, wherein the biological sample includes sperm and the at least one pathogen includes at least one of a virus and bacteria.

12. The method as described in claim 11, wherein the biological sample includes somatic cells.

* * * * *